US006344213B1

(12) United States Patent
Leone-Bay et al.

(10) Patent No.: US 6,344,213 B1
(45) Date of Patent: Feb. 5, 2002

(54) COMPOUNDS AND COMPOSITIONS FOR DELIVERING ACTIVE AGENTS

(75) Inventors: Andrea Leone-Bay, Ridgefield, CT (US); Sam J. Milstein, Larchmont, NY (US); Donald J. Sarrubi, Bronxville, NY (US); Harry Leipold, Elmsford, NY (US)

(73) Assignee: Emisphere Technologies, Inc., Tarrytown, NY (US)

( * ) Notice: Subject to any disclaimer, the term of this patent is extended or adjusted under 35 U.S.C. 154(b) by 0 days.

(21) Appl. No.: 08/820,694

(22) Filed: Mar. 18, 1997

Related U.S. Application Data
(60) Provisional application No. 60/017,902, filed on Mar. 29, 1996.

(51) Int. Cl.[7] .............................. A61K 9/20; A61K 9/48
(52) U.S. Cl. .................... 424/451; 424/464; 424/465; 424/452; 424/455; 424/489
(58) Field of Search ................ 424/451, 464, 424/465, 489, 452, 455, 456

(56) References Cited

U.S. PATENT DOCUMENTS

| 3,795,739 A | 3/1974 | Birkmayer et al. | 424/274 |
|---|---|---|---|
| 3,939,253 A | 2/1976 | Sloan et al. | 424/309 |
| 4,035,507 A | 7/1977 | Bodor et al. | 424/311 |
| 4,061,466 A | 12/1977 | Sjoholm et al. | 424/311 |
| 4,147,767 A | 4/1979 | Yapel, Jr. | 424/22 |
| 4,238,506 A | 12/1980 | Heerdt et al. | 424/319 |
| 4,239,754 A | 12/1980 | Sache et al. | 424/183 |
| 4,393,192 A | 7/1983 | Coffey et al. | 528/292 |
| 4,442,090 A | 4/1984 | Nishimura et al. | 424/178 |
| 4,462,991 A | 7/1984 | Higuchi et al. | 424/177 |
| 4,499,299 A | 2/1985 | Bernstein et al. | 514/570 |
| 4,654,327 A | 3/1987 | Teng | 514/56 |
| 4,656,161 A | 4/1987 | Herr | 514/56 |
| 4,692,433 A | 9/1987 | Hostetler et al. | 514/12 |
| 4,757,066 A | 7/1988 | Shiokari et al. | 514/210 |

(List continued on next page.)

FOREIGN PATENT DOCUMENTS

| EP | 0036145 | 9/1981 | |
| EP | 226223 A2 | 6/1987 | ......... C07C/103/46 |
| EP | 226223 | 6/1987 | |
| EP | 0365183 | 10/1989 | |
| EP | 0517211 | 9/1992 | |
| EP | 0576941 | 6/1993 | |
| ES | 369853 | 7/1969 | |
| GB | 2095994 | 10/1982 | |
| JP | 2239980 | 9/1990 | .................... 35/84 |
| WO | 9747270 | 12/1997 | |

(List continued on next page.)

OTHER PUBLICATIONS

Picciola G.: "Sintesi Di Acidi Chiazolinioici E Benzoassazinonici E Studio Delle Loro Proprieta Antiniammatorie" IT, Societa Chimica Italiana Pavia vol.31, No. 9 pp. 655–664 and English Translation.
Chem Abs 73548–12–6 (Apr. 1991).
Chem Abs 70204–54–5 (Apr. 1991).
Chem Abs 184360 –83–342 (1975) Solubility and disassociation constants of some alicyclic acids.
Chemical Abstract, vol. 99(23) Abst. No. 191473h (1983).
Riveria, Theresa M. et al. "Oral Delivery of Heparin in Combination with Sodium N–[8–2–hydroxybenzoyl)amino] caprylate: Pharmacological Considerations" Pharamceutical Research vol 14(12) 1830–1834 (1997).

(List continued on next page.)

Primary Examiner—James M. Spear
(74) Attorney, Agent, or Firm—Darby & Darby

(57) ABSTRACT

Modified amino acid compounds useful in the delivery of active agents are provided. Methods of administration and preparation are provided as well.

54 Claims, 3 Drawing Sheets

U.S. PATENT DOCUMENTS

| | | | |
|---|---|---|---|
| 4,835,312 A | 5/1989 | Itoh et al. ................... | 564/205 |
| 4,873,087 A | 10/1989 | Morishita et al. ........... | 424/433 |
| 4,878,942 A | 11/1989 | Motegi et al. ................ | 71/109 |
| 4,900,730 A | 2/1990 | Miyauchi ..................... | 514/12 |
| 4,927,928 A | 5/1990 | Shroot et al. ............... | 544/154 |
| 5,066,487 A | 11/1991 | Morelle et al. ............... | 424/68 |
| 5,352,461 A | 10/1994 | Feldstein et al. ............ | 424/493 |
| 5,447,728 A | 9/1995 | Milstein et al. ............. | 424/490 |
| 5,451,410 A | 9/1995 | Milstein et al. ............. | 424/490 |
| 5,541,155 A | 7/1996 | Leone-Bay et al. ............ | 514/2 |
| 5,629,020 A | 5/1997 | Leone-Bay et al. ......... | 424/489 |
| 5,643,957 A | 7/1997 | Leone-Bay et al. ......... | 514/563 |
| 5,650,386 A | 7/1997 | Leone-Bay et al. ............ | 514/2 |
| 5,665,700 A | 9/1997 | Cho et al. ...................... | 514/2 |
| 5,693,338 A | 12/1997 | Milstein ..................... | 424/451 |
| 5,705,529 A | 1/1998 | Matyus et al. ............... | 514/541 |
| 5,709,861 A | 1/1998 | Santiago et al. ......... | 424/184.1 |
| 5,714,167 A | 2/1998 | Hilstein et al. ............. | 424/490 |
| 5,750,147 A | 5/1998 | Kantor ........................ | 424/491 |
| 5,766,633 A | 6/1998 | Hilstein et al. ............. | 424/489 |
| 5,773,647 A | 6/1998 | Leone-Bay et al. ......... | 562/444 |
| 5,792,451 A | 8/1998 | Sarubbi et al. ............. | 424/85.4 |
| 5,811,127 A | 9/1998 | Milstein et al. ............. | 424/490 |
| 5,863,944 A | 1/1999 | Leone-Bay et al. ......... | 514/559 |
| 5,866,536 A | 2/1999 | Leone-Bay et al. ............ | 514/2 |
| 5,958,457 A | 9/1999 | Santiago et al. ............ | 424/490 |
| 5,990,166 A | 11/1999 | Leone-Bay et al. ......... | 514/563 |
| 6,001,347 A | 12/1999 | Leone-Bay et al. ......... | 424/85.1 |
| 6,051,258 A | 4/2000 | Kantor ........................ | 424/491 |
| 6,051,561 A | 4/2000 | Leone-Bay et al. ........... | 514/56 |
| 6,060,513 A | 5/2000 | Leone-Bay et al. ......... | 514/559 |
| 6,071,510 A | 6/2000 | Leone-Bay et al. ......... | 424/85.2 |
| 6,071,538 A | 6/2000 | Milstein et al. ............. | 424/464 |
| 6,090,958 A | 7/2000 | Leone-Bay et al. ......... | 554/112 |
| 6,099,856 A | 8/2000 | Milstein et al. ............. | 424/450 |

FOREIGN PATENT DOCUMENTS

| | | |
|---|---|---|
| WO | WO 97/47270 | 12/1997 |
| WO | WO 97/47288 | 12/1997 |
| WO | 8807378 | 10/1998 |
| WO | 0006184 | 2/2000 |
| WO | 0006534 | 2/2000 |
| WO | 0048589 | 8/2000 |
| WO | 0009390 | 10/2000 |

OTHER PUBLICATIONS

Leone–Bay, A. et al. "The evolution of an oral heparin dosing solution" Drugs of the Future vol 22(8) 885–891 (1997).

Brayden, D. et al. "Heparin Absorption across the intestin: Effects of Sodium N–[8–2hydorxybenzoyl)Amino] Caprylate in rat in situ intestinal instillations ind in Caco–2 monolayers" Pharmaceutical Research vol. 14(12) 1772–1779 (1997).

Leone–Bay, A. "Acylated non–alpha–amino acids as novle agents for the oral delivery of heparin sodium, USP" Journal of Controlled Release 50:41–49 (1998).

Leone–Bay, A. "4–[4–(2–Hydroxybenzoyl) amino]phenyl–butyric Acid as Novel Oral Delivery Agent for Recombinant Human Growth Hormone"; Journal of Medicinal Chemistry vol.39, No. 13 pp 2571–2578 (1996).

Leone–Bay, A. "N–Acylated alpha–amino acids as novel oral delivery agents for proteins" ;Journal of Medicinal Chemistry vol 38, 4263–4269 (1995).

Leone–Bay, A. "N–Acylated alpha–amino acids as novel oral delivery agents for proteins" ;Journal of Medicinal Chemistry vol 38, 4257–4262 (1995).

Ho Koc–Kan; et al. "A Practial Synthesis of ω–aminoalkanoic acid derivatives form Cycloalkanones" Synthetic Communication, vol. 26, No. 14:2641–2649 (1996).

Gurrieri and Siracusa: "Thermal Condensation of Some alpha–aminoacids with Phatalic Acid" Thermochimica Acta, 7 (1973) 231–239.

Amino Yusuke et al. Chem Pharm Bull 36 pp. 4426–4434 (1988).

Brown et al., *J. Med Chem.* 27:79–81 (1984).

Johansen, Marianne, et al. "The Kinetics of decompn. Of various N–Mannich bases of salicylamide" Int. J. Pharm. (1980), 7(2):119–27 (1980).

Chemical Abstracts, Registry No. 73548–12–6 (Apr. 1991).

Chemical Abstracts, Registry No. 70204–54–5 (Apr. 1991).

G. Picciola, Il Farmaco, 31:655–664 (1976).

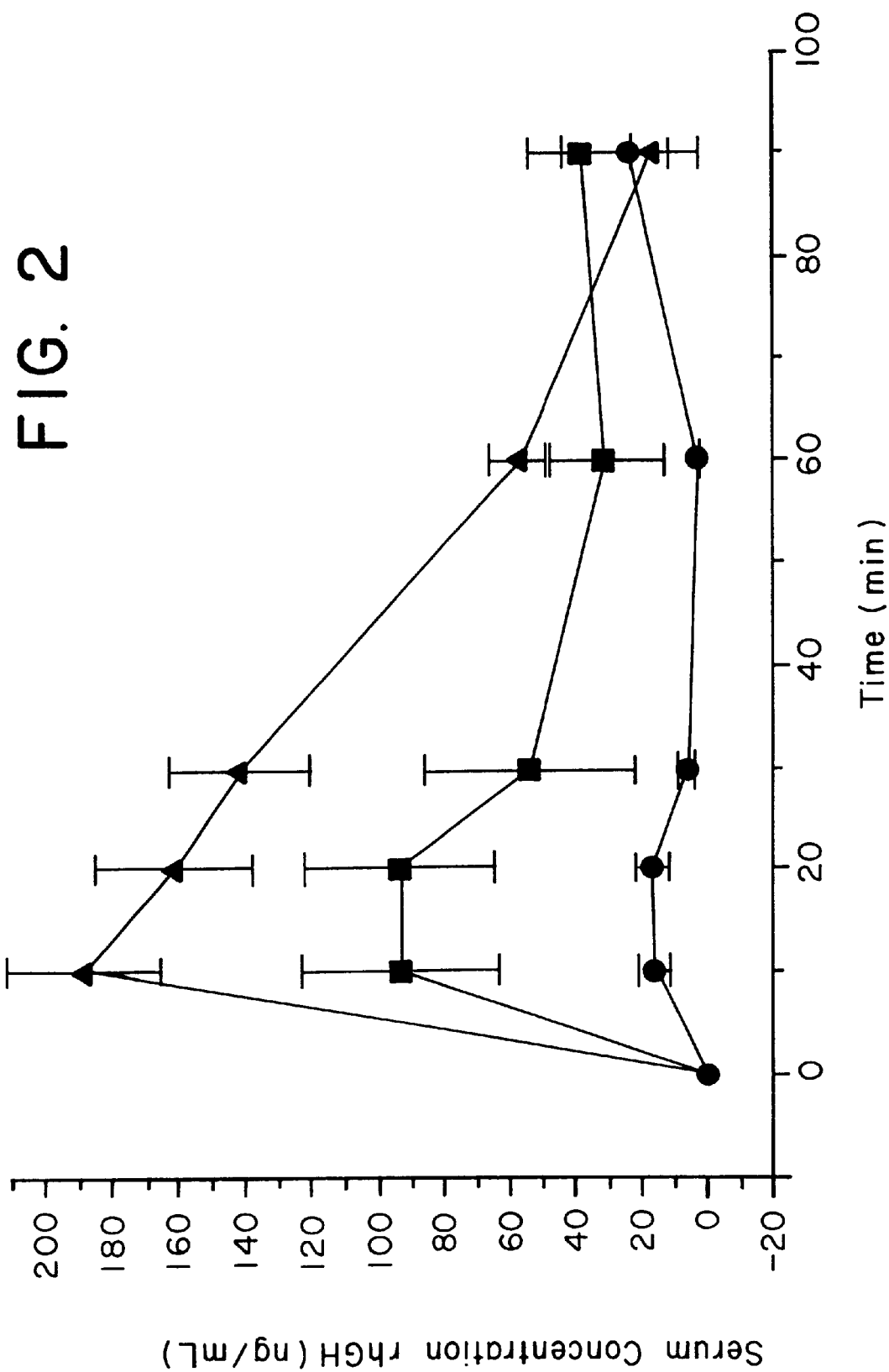

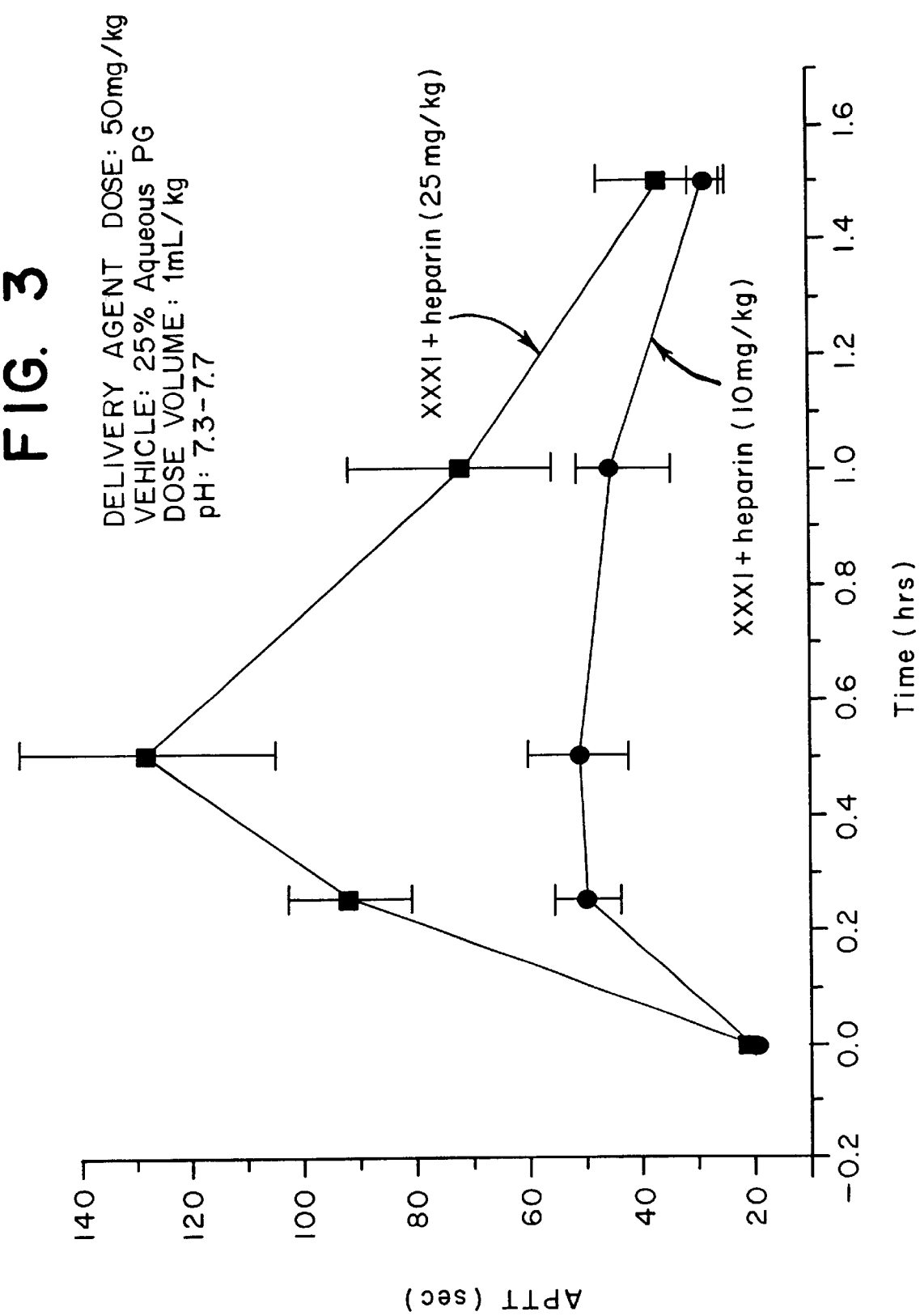

COMPOUNDS AND COMPOSITIONS FOR DELIVERING ACTIVE AGENTS

The present application is based upon one Provisional Patent Application Ser. No. 60/017,902 filed Mar. 29, 1996. Applicant claims the benefit of the filing dates of the aforesaid provisional application under 35 U.S.C. §119. This application also claims priority from International Application No. PCT/US96/04580, published as WO 96/30036 on Oct. 3, 1996, which claims priority from U.S. Ser. No. 08/414,654 filed Mar. 31, 1995, now U.S. Pat. No. 5,650,386, and U.S. Ser. No. 60/003,111 filed Sep. 1, 1995, now abandoned.

FIELD OF THE INVENTION

The present invention relates to compounds for delivering active agents, and particularly biologically or chemically active agents such as, for example, bioactive peptides and the like. These compounds are used as carriers to facilitate the delivery of a cargo to a target. The carriers are modified amino acids and are well suited to form non-covalent mixtures with biologically-active agents for oral administration to animals. Methods for the preparation and for the administration of such compositions are also disclosed.

BACKGROUND OF THE INVENTION

Conventional means for delivering active agents are often severely limited by biological, chemical, and physical barriers. Typically, these barriers are imposed by the environment through which delivery occurs, the environment of the target for delivery, or the target itself.

Biologically or chemically active agents are particularly vulnerable to such barriers. For example in the delivery to animals of pharmacological and therapeutic agents, barriers are imposed by the body. Examples of physical barriers are the skin and various organ membranes that must be traversed before reaching a target. Chemical barriers include, but are not limited to, pH variations, lipid bi-layers, and degrading enzymes.

These barriers are of particular significance in the design of oral delivery systems. Oral delivery of many biologically or chemically active agents would be the route of choice for administration to animals if not for biological, chemical, and physical barriers such as varying pH in the gastro-intestinal (GI) tract, powerful digestive enzymes, and active agent impermeable gastro-intestinal membranes. Among the numerous agents which are not typically amenable to oral administration are biologically or chemically active peptides, such as calcitonin and insulin; polysaccharides, and in particular mucopolysaccharides including, but not limited to, heparin; heparinoids; antibiotics; and other organic substances. These agents are rapidly rendered ineffective or are destroyed in the gastro-intestinal tract by acid hydrolysis, enzymes, or the like.

Earlier methods for orally administering vulnerable pharmacological agents have relied on the co-administration of adjuvants (e.g., resorcinols and non-ionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation.

Liposomes have also been described as drug delivery systems for insulin and heparin. See, for example, U.S. Pat. No. 4,239,754; Patel et al. (1976), *FEBS Letters*, Vol. 62, pg. 60; and Hashimoto et al. (1979), *Endocrinology Japan*, Vol. 26, pg. 337.

However, broad spectrum use of such drug delivery systems is precluded because: (1) the systems require toxic amounts of adjuvants or inhibitors; (2) suitable low molecular weight cargos, i.e. active agents, are not available; (3) the systems exhibit poor stability and inadequate shelf life; (4) the systems are difficult to manufacture; (5) the systems fail to protect the active agent (cargo); (6) the systems adversely alter the active agent; or (7) the systems fail to allow or promote absorption of the active agent.

More recently, microspheres of artificial polymers of mixed amino acids (proteinoids) have been used to deliver pharmaceuticals. For example, U.S. Pat. No. 4,925,673 describes drug-containing proteinoid microsphere carriers as well as methods for their preparation and use. These proteinoid microspheres are useful for the delivery of a number of active agents.

There is still a need in the art for simple, inexpensive delivery systems which are easily prepared and which can deliver a broad range of active agents.

SUMMARY OF THE INVENTION

Compositions which are useful in the delivery of active agents are provided. These compositions include at least one active agent, and eferably a biologically or chemically active agent, and at least one of the following compounds I–CXXIII, or salts thereof.

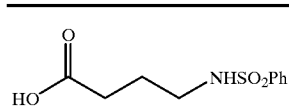

I

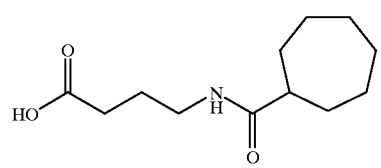

II

-continued
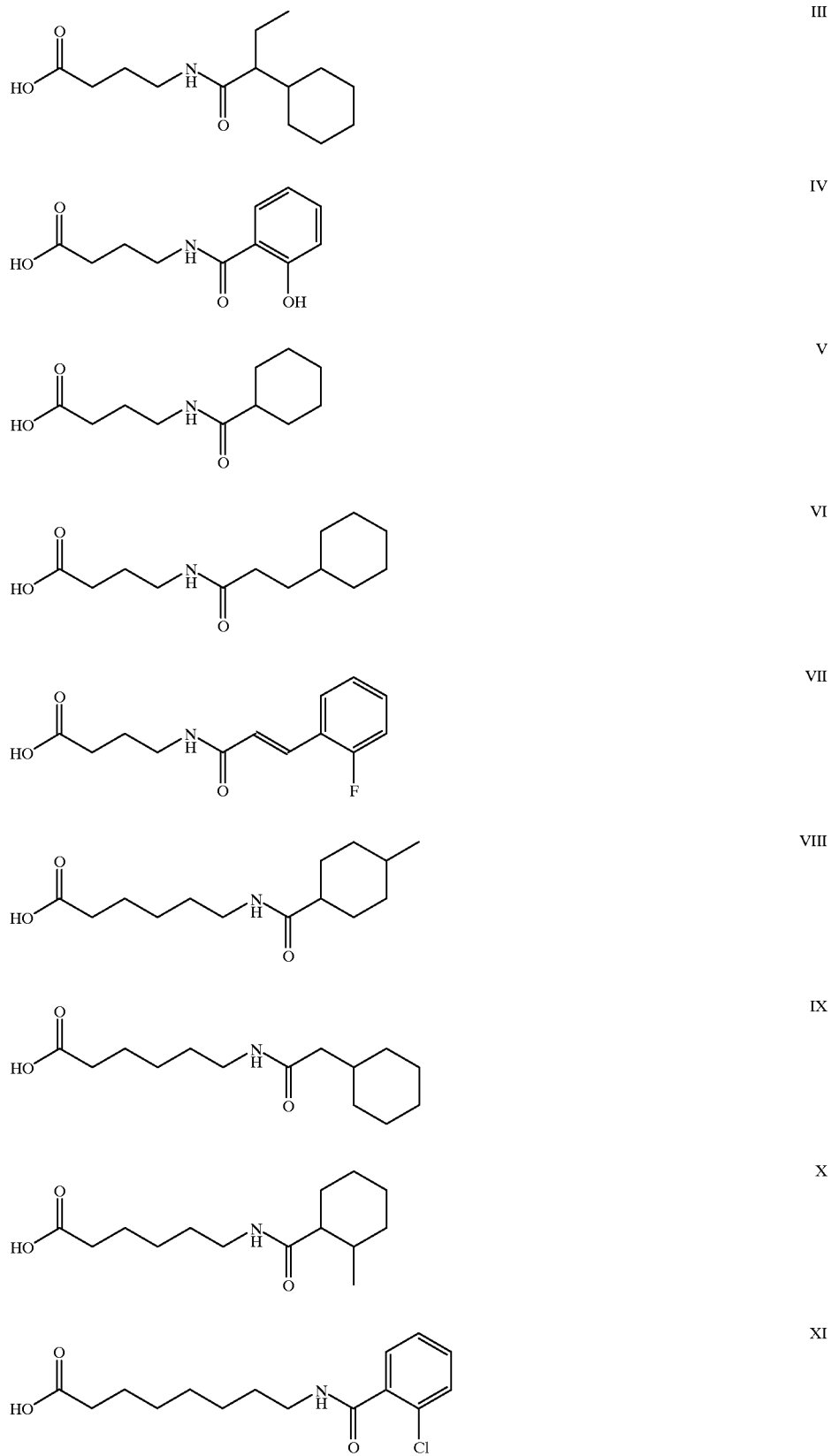

-continued
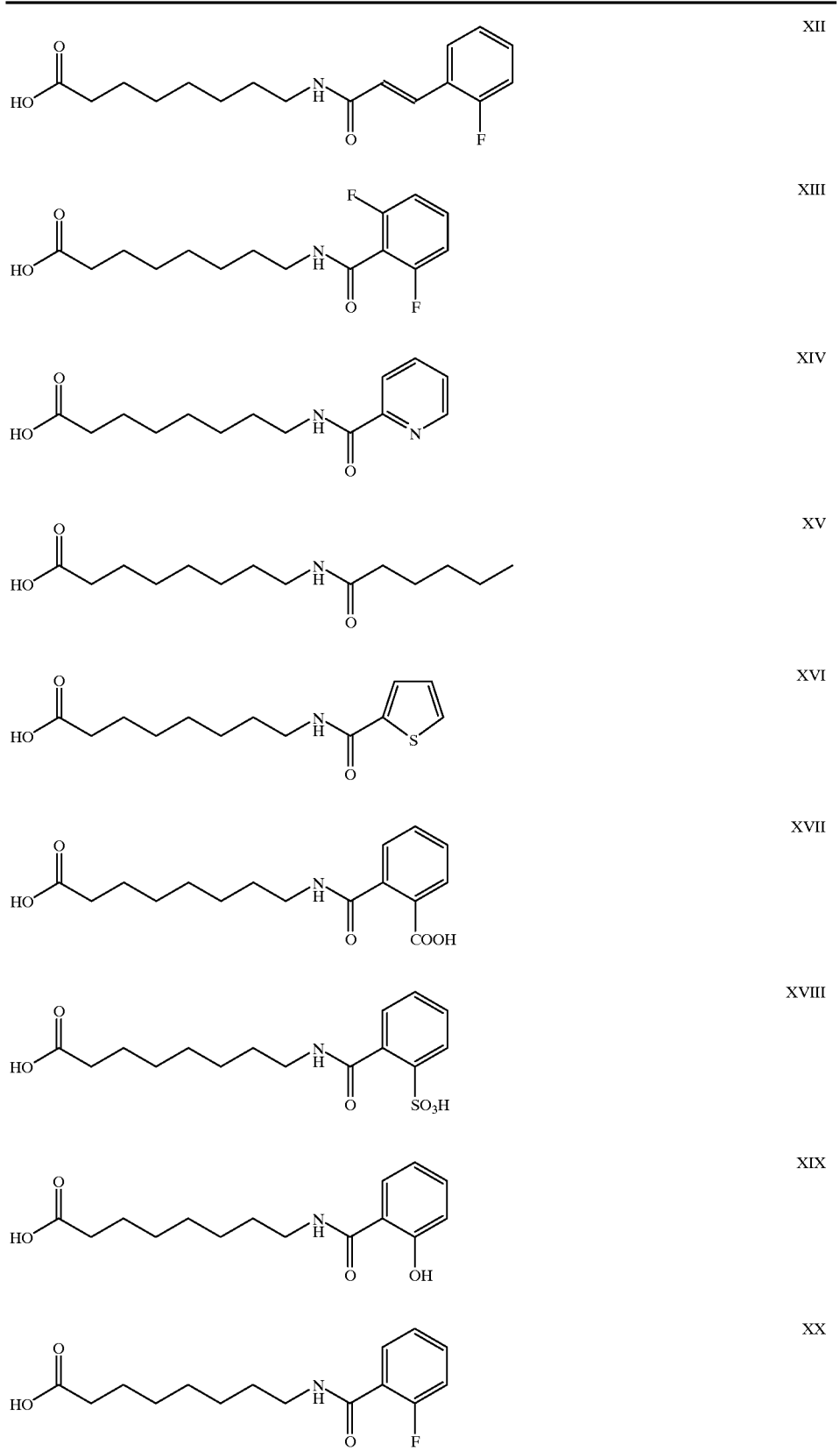

-continued
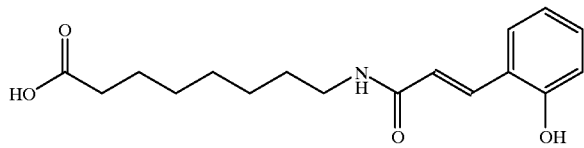
XXI
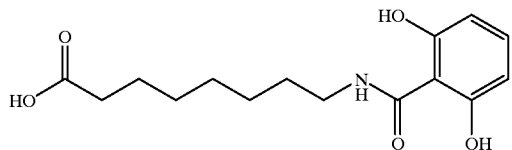
XXII
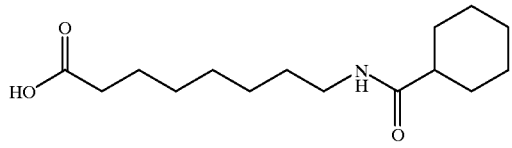
XXIII
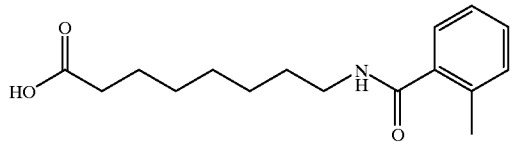
XXIV
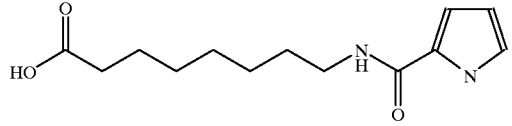
XXV
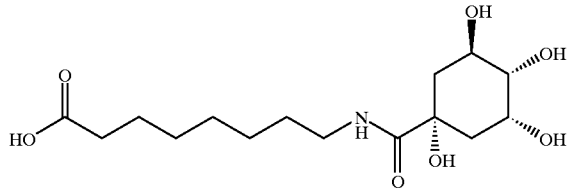
XXVI
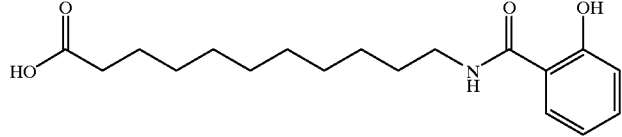
XXVII
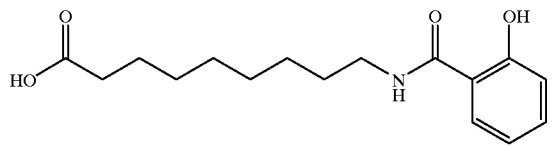
XXVIII
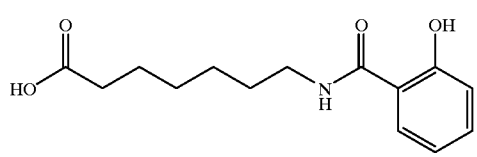
XXIX -continued
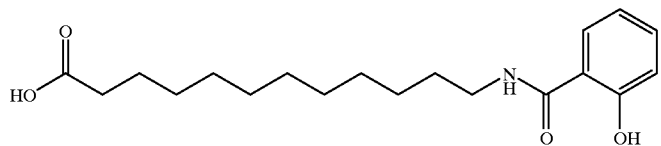 XXX
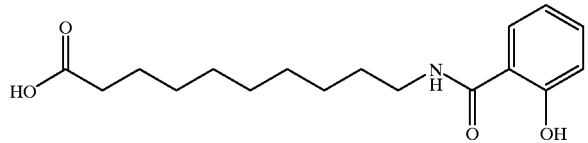 XXXI
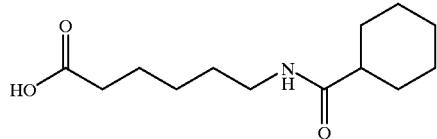 XXXII
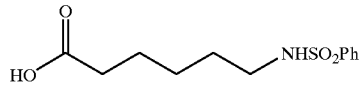 XXXIII
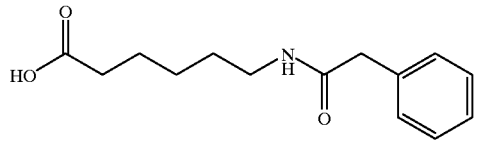 XXXIV
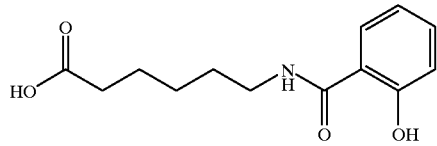 XXXV
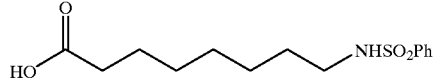 XXXVI
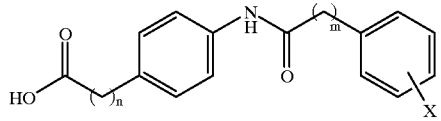 A
| Compound | n | m | X |
|---|---|---|---|
| XXXVII | 0 | 0 | 4-Cl |
| XXXVIII | 3 | 0 | H |
| XXXIX | 3 | 1 | 4-CH$_3$ |
| XL | 3 | 1 | 2-F |
| XLI | 3 | 1 | 2-CH$_3$ |
| XLII | 3 | 0 | 3-CF$_3$ |
| XLIII | 3 | 4 | H |
| XLIV | 3 | 0 | 3-Cl |
| XLV | 3 | 0 | 3-F |
| XLVI | 3 | 0 | 3-CH$_3$ |
| XLVII | 0 | 0 | 2-CF$_3$ |
| XLVIII | 1 | 2 | H |
| XLIX | 3 | 2 | 2-F |
| L | 3 | 0 | 3,4-OCH$_2$O— |
| LI | 3 | 0 | 2-COOH |
| LII | 1 | 0 | 2-OH |
| LIII | 3 | 0 | 2,6-dihydroxy |
| LIV | 2 | 0 | 2-OH |

-continued

| | | | |
|---|---|---|---|
| LV | 0 | 0 | 2,4-difluoro |
| LVI | 2 | 0 | 2,6-dihydroxy |
| LVII | 0 | 0 | 4-CF$_3$ |
| LVIII | 3 | 0 | 3-NMe$_2$ |
| LIX | 2 | 0 | 3-NMe$_2$ |
| LX | 3 | 0 | 2,6-dimethyl |
| LXI | 3 | 0 | 2-NO$_2$ |
| LXII | 3 | 0 | 2-CF$_3$ |
| LXIII | 3 | 0 | 4-n-Pr |
| LXIV | 3 | 0 | 2-NH$_2$ |
| LXV | 3 | 0 | 2-OCH$_3$ |
| LXVI | 3 | 0 | 3-NO$_2$ |
| LXVII | 3 | 0 | 3-NH$_2$ |
| LXVIII | 2 | 0 | 2-NO$_2$ |
| LXIX | 2 | 0 | 2-NH$_2$ |
| LXX | 3 | 0 | 2-OCF$_3$ |
| LXXI | 2 | 0 | 2-OCH$_3$ |
| LXXII | 2 | 0 | 2-OCF$_3$ |

B

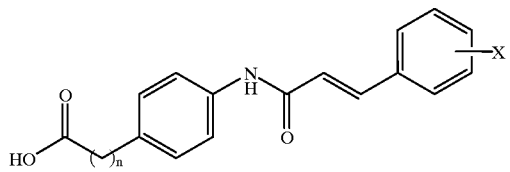

| Compound | n | X |
|---|---|---|
| LXXIII | 3 | 4-CF$_3$ |
| LXXIV | 1 | 2-F |
| LXXV | 1 | 4-CF$_3$ |
| LXXVI | 3 | 3,4-dimethoxy |
| LXXVII | 0 | 3-OCH$_3$ |
| LXXVIII | 3 | 3-OCH$_3$ |
| LXXIX | 3 | 2,6-difluoro |
| LXXX | 3 | 4-CH$_3$ |
| LXXXI | 1 | 4-OCH$_3$ |
| LXXXII | 2 | 2-F |
| LXXXIII | 0 | 2-F |
| LXXXIV | 2 | 4-OCH$_3$ |
| LXXXV | 0 | 2-OCH$_3$ |
| LXXXVI | 2 | 2-OCH$_3$ |
| LXXXVII | 0 | 4-CF$_3$ |
| LXXXVIII | 3 | 3-F |
| LXXXIX | 3 | 2-OCH$_3$ |

C

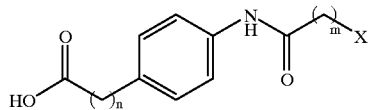

| Compound | n | m | X |
|---|---|---|---|
| XC | 3 | 0 | 2-carboxycyclohexyl |
| XCI | 3 | 3 | cyclohexyl |
| XCII | 3 | 0 | 2-adamantyl |
| XCIII | 3 | 0 | 1-morpholino |

D

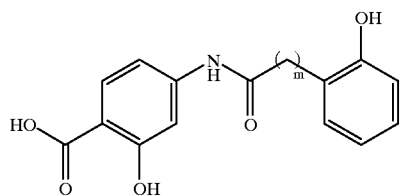

| Compound | m |
|---|---|
| XCIV | 0 |
| XCV | 3 |

-continued
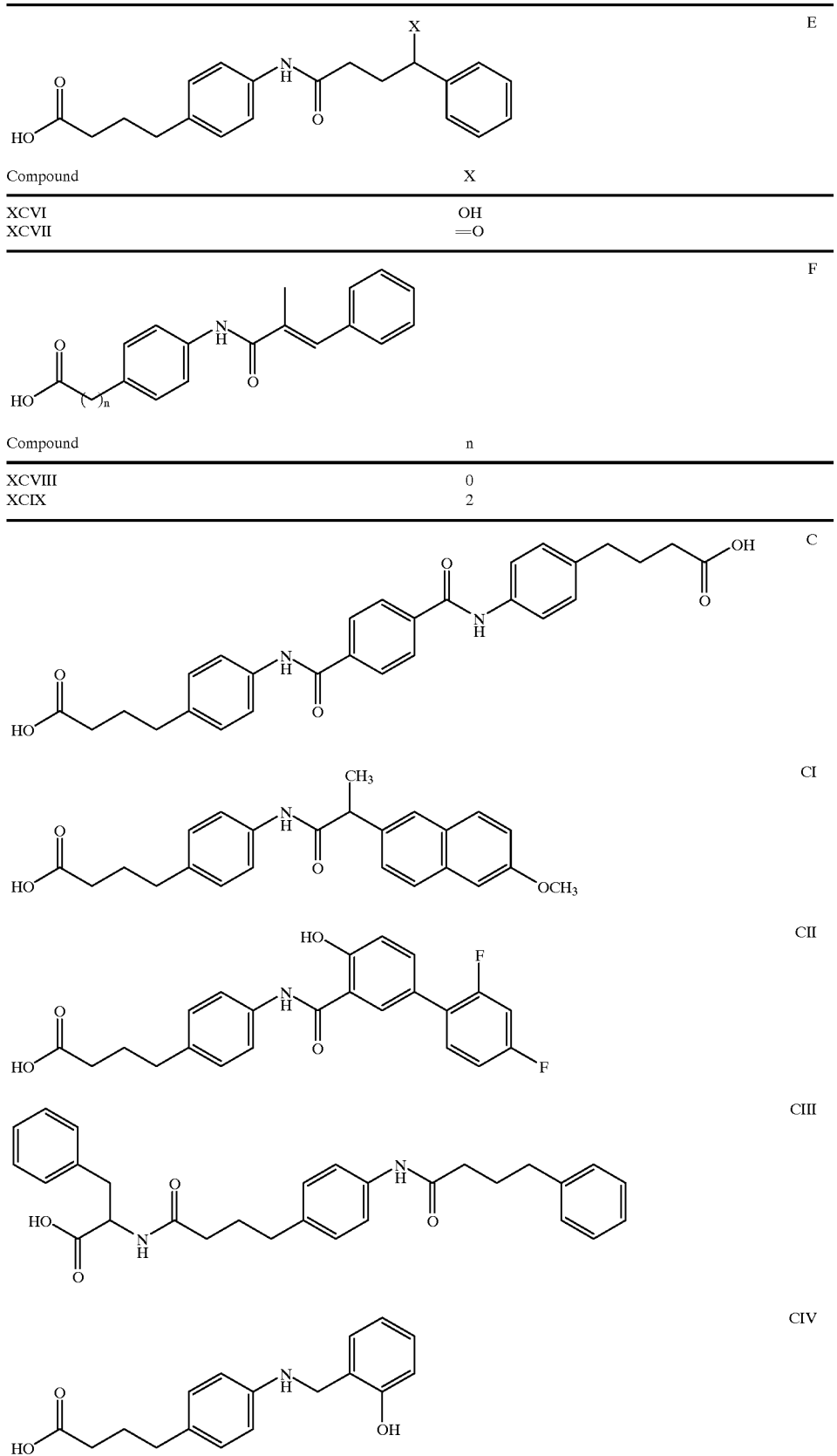

-continued
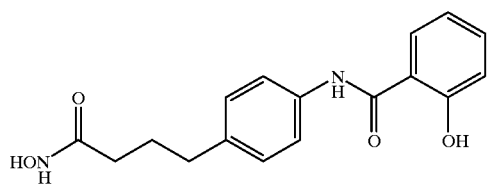
CV
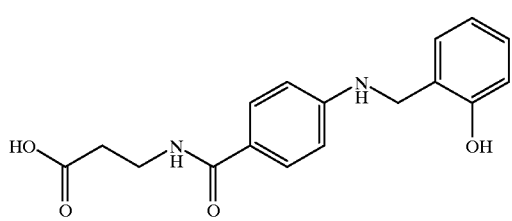
CVI
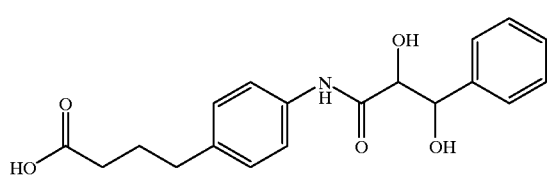
CVII
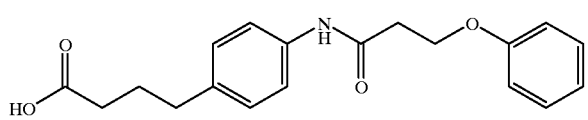
CVIII
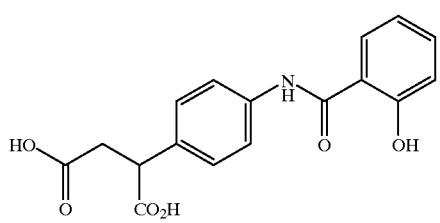
CIX
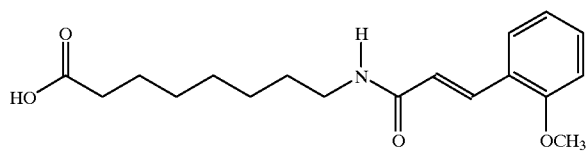
CX
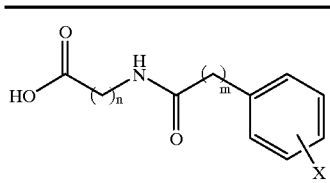
G
| Compound | n | m | X |
|---|---|---|---|
| CXI | 6 | 0 | 2-OH |
| CXII | 7 | 3 | H |
| CXIII | 7 | 0 | 2-I |
| CXIV | 7 | 0 | 2-Br |
| CXV | 7 | 0 | 3-NO$_2$ |
| CXVI | 7 | 0 | 3-N(CH$_3$)$_2$ |
| CXVII | 7 | 0 | 2-NO$_2$ |
| CXVIII | 7 | 0 | 4-NO$_2$ |
| CXIX | 9 | 0 | 2-OH |

-continued

| Compound | X |
|---|---|
| CXX | 1-morpholino |
| CXXI | O-t-Butyl |
| CXXII | CH(CH$_2$Ph)NC(O)O-t-Bu |
| CXXIII | 2-hydroxyphenyl |

It has been discovered that organic acid compounds, and their salts, having an aromatic amide group, having a hydroxy group substituted in the ortho position on the aromatic ring, and a lipophilic chain with from about 4 carbon atoms to about 20 atoms in the chain are useful as carriers for the delivery of active agents. In a preferred form the lipophilic chain can have from 5 to 20 carbon atoms.

Compositions comprising the carrier compounds discussed above and active agents have been shown effective in delivering active agents to selected biological systems. These compositions include at least one active agent which is preferably a biologically or chemically active agent, and at least one carrier compound having the formula:

2-HO—Ar—CONR$^8$—R$^7$—COOH wherein Ar is a substituted or unsubstituted phenyl or naphthyl;

R$^7$ is selected from the group consisting of C$_4$ to C$_{20}$ alkyl, C$_4$ to C$_{20}$ alkenyl, phenyl, naphthyl, (C$_1$ to C$_{10}$ alkyl)phenyl, (C$_1$ to C$_{10}$ alkenyl)phenyl, (C$_4$ to C$_{10}$ alkyl)naphthyl, (C$_1$ to C$_{10}$ alkenyl)naphthyl, phenyl (C$_1$ to C$_{10}$ alkyl), phenyl (C$_1$ to C$_{10}$ alkenyl), naphthyl (C$_1$ to C$_{10}$ alkyl), and naphthyl (C$_1$ to C$_{10}$ alkenyl);

R$^8$ is selected from the group consisting of hydrogen, C$_1$ to C$_4$ alkyl, C$_1$ to C$_4$ alkenyl, hydroxy, and C$_1$ to C$_4$ alkoxy;

R$^7$ is optionally substituted with C$_1$ to C$_4$ alkyl, C$_1$ to C$_4$ alkenyl, C$_1$ to C$_4$ alkoxy, —OH, —SH and —CO$_2$R$^9$ or any combination thereof;

R$^9$ is hydrogen, C$_1$ to C$_4$ alkyl or C$_1$ to C$_4$ alkenyl;

R$^7$ is optionally interrupted by oxygen, nitrogen, sulfur or any combination thereof;

with the proviso that the compounds are not substituted with an amino group in the position alpha to the acid group, or salts thereof.

The preferred R$^7$ groups are of C$_4$ to C$_{20}$ alkyl and C$_4$ to C$_{20}$ alkenyl. The most preferred R$^7$ groups are C$_5$ to C$_{20}$ alkyl and C$_5$ to C$_{20}$ alkenyl.

A preferred carrier compound can have the formula:

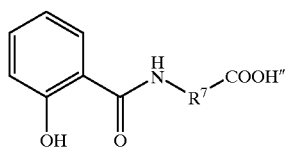

wherein R$^7$ is defined above.

Further contemplated by the present invention are dosage unit forms that include these compositions.

Also contemplated is a method for preparing these compositions which comprises mixing at least one active agent with at least one compound as described above, and optionally, a dosing vehicle.

In an alternative embodiment, these non-toxic compounds are orally administered to animals as part of a delivery system by blending or mixing the compounds with an active agent prior to administration.

Further provided is a method for the preparation of a compound having the formula:

CXXIV

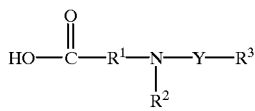

wherein

Y is C or $$\overset{O}{\underset{\|}{SO_2}};$$

R$^1$ is C$_3$–C$_{24}$ alkyl, C$_2$–C$_{20}$ alkenyl, C$_2$–C$_{20}$ alkyne, cycloalkyl, or aromatic;

R$^2$ is hydrogen, C$_1$–C$_4$ alkyl, or C$_2$–C$_4$ alkenyl; and

R$^3$ is C$_1$–C$_7$ alkyl, C$_3$–C$_{10}$ cycloalkyl, aryl, thienyl, pyrrolo, or pyridyl, where R$^3$ is optionally substituted by one or more C$_1$–C$_5$ alkyl group, C$_2$–C$_4$ alkenyl group, F, Cl, OH, SO$_2$, COOH, or SO$_3$H; said method comprising (a) reacting in water and the presence of a base, a compound having the formula:

CXXV

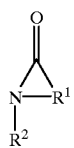

with a compound having the formula:

wherein

Y, R$^1$, R$^2$, and R$^3$ are as above and X is a leaving group.

DESCRIPTION OF THE DRAWINGS

FIG. 2 is a graphic illustration of the results of Sublingual (SL), intranasal (IN), and intracolonic (IC) dosing of rhGH in rats.

FIG. 3 is a graphic illustration of the results of intracolonic dosing of delivery of heparin with compound XXXI carrier.

DETAILED DESCRIPTION OF THE INVENTION

Figure 1:
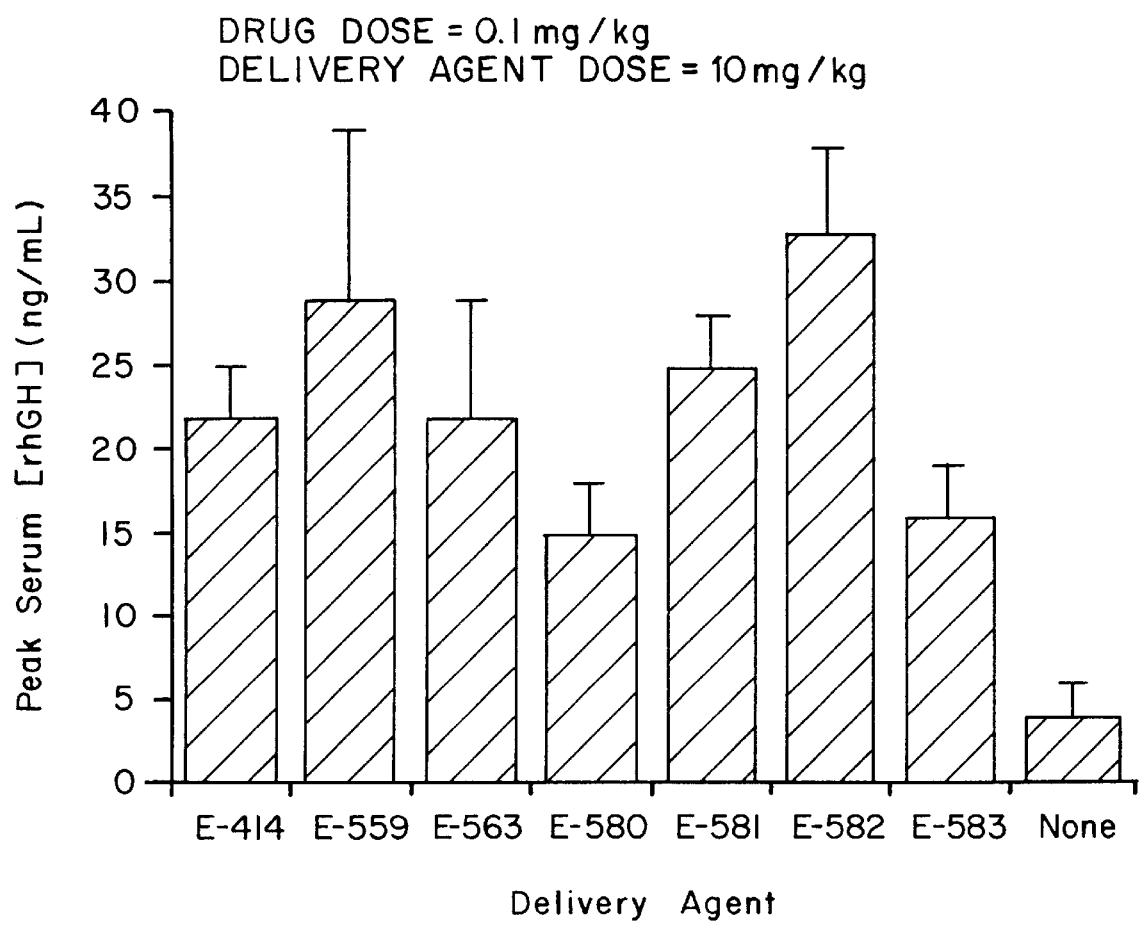
FIG. 1 is a graphic illustration of the results of subcutaneous injection of rhGH composition in rats.

The specific compositions of the present invention include an active agent and a modified amino acid. These compositions may be used to deliver various active agents through various biological, chemical, and physical barriers and are particularly suited for delivering active agents which are subject to environmental degradation. The compositions of the subject invention are particularly useful for delivering or administering biologically or chemically active agents to any animals such as birds; mammals, such as primates and particularly humans; and insects.

Other advantages of the present invention include the use of easy to prepare, inexpensive raw materials. The compositions and the formulation methods of the present invention are cost effective, simple to perform, and amenable to industrial scale up for commercial production.

Subcutaneous, sublingual, and intranasal coadministration of an active agent, such as recombinant human growth hormone (rhGH), and the delivery agents, and particularly proteins, described herein results in an increased bioavailability of the active agent compared to administration of the active agent alone. A similar result is obtained by coadministration of salmon calcitonin with the delivery agents, in rats. Data supporting these findings are presented in the examples.

Active Agents

Active agents suitable for use in the present invention include biologically or chemically active agents, chemically active agents, including, but not limited to, fragrances, as well as other active agents such as, for example, cosmetics.

Biologically or chemically active agents include, but are not limited to, pesticides, pharmacological agents, and therapeutic agents. For example, biologically or chemically active agents suitable for use in the present invention include, but are not limited to, peptides, and particularly small peptides; hormones, and particularly hormones which by themselves do not or only a fraction of the administered dose passes through the gastrointestinal mucosa and/or are susceptible to chemical cleavage by acids and enzymes in the gastrointestinal tract; polysaccharides, and particularly mixtures of muco-polysaccharides; carbohydrates; lipids; or any combination thereof. Further examples include, but are not limited to, human growth hormones; bovine growth hormones; growth releasing hormones; interferons; interleukin-II; insulin; heparin, and particularly low molecular weight heparin; calcitonin; erythropoietin; atrial naturetic factor; antigens; monoclonal antibodies; somatostatin; adrenocorticotropin, gonadotropin releasing hormone; oxytocin; vasopressin; cromolyn sodium (sodium or disodium chromoglycate); vancomycin; desferrioxamine (DFO); parathyroid hormone; anti-microbials, including, but not limited to anti-fungal agents; or any combination thereof.

Modified Amino Acids

The terms modified amino acid, modified poly amino acid, and modified peptide are meant to include amino acids which have been modified, or poly amino acids and peptides in which at least one amino acid has been modified, by acylating or sulfonating at least one free amine group with an acylating or sulfonating agent which reacts with at least one of the free amine groups present.

Amino acids, poly amino acids, and peptides, in modified form, may be used to deliver active agents including, but not limited to, biologically or chemically active agents such as for example, pharmacological and therapeutic agents.

An amino acid is any carboxylic acid having at least one free amine group and includes naturally occurring and synthetic amino acids.

Poly amino acids are either peptides or two or more amino acids linked by a bond formed by other groups which can be linked, e.g. an ester, anhydride, or an anhydride linkage.

Peptides are two or more amino acids joined by a peptide bond. Peptides can vary in length from dipeptides with two amino acids to poly peptides with several hundred amino acids. See *Chambers Biological Dictionary*, editor Peter M. B. Walker, Cambridge, England: Chambers Cambridge, 1989, page 215. Special mention is made of di-peptides, tri-peptides, tetra-peptides, and penta-peptides.

Although compounds I–CXXIII above have been found to act as carriers for the oral delivery of biologically or chemically active agents, special mention is made of compounds I–XXXI above.

Modified amino acids are typically prepared by modifying the amino acid or an ester thereof. Many of these compounds are prepared by acylation or sulfonation with agents having the formula:

$$X—Y—R^4$$

wherein:

$R^4$ is the appropriate radical to yield the modification indicated in the final product, Y is C 

and X is a leaving group. Typical leaving groups include, but are not limited to, halogens such as, for example, chlorine, bromine, and iodine. Additionally, the corresponding anhydrides are modifying agents.

Many of the compounds of the present invention can be readily prepared from amino acids by methods within the skill of those in the art based upon the present disclosure. For example, compounds I–VII are derived from aminobutyric acid; Compounds VIII–X and XXXII–XXXV are derived from aminocaproic acid; and Compounds XI–XXVI and XXXVI are derived from aminocaprylic acid. For example, the modified amino acid compounds above may be prepared by reacting the single amino acid with the appropriate modifying agent which reacts with free amino moiety present in the amino acids to form amides. Protecting groups may be used to avoid unwanted side reactions as would be known to those skilled in the art.

The amino acid can be dissolved in aqueous alkaline solution of a metal hydroxide, e.g., sodium or potassium hydroxide, and heated at a temperature ranging between about 5° C. and about 70° C., preferably between about 10° C. and about 40° C., for a period ranging between about 1 hour and about 4 hours, preferably about 2.5 hours. The amount of alkali employed per equivalent of NH$_2$ groups in the amino acid generally ranges between about 1.25 and about 3 mmole, preferably between about 1.5 and about 2.25 mmole per equivalent of $NH_2$. The pH of the solution generally ranges between about 8 and about 13, preferably ranging between about 10 and about 12.

Thereafter, the appropriate amino modifying agent is added to the amino acid solution while stirring. The temperature of the mixture is maintained at a temperature generally ranging between about 5° C. and about 70° C., preferably between about 10° C. and about 40° C., for a period ranging between about 1 and about 4 hours. The amount of amino modifying agent employed in relation to the quantity of amino acid is based on the moles of total free $NH_2$ in the amino acid. In general, the amino modifying agent is employed in an amount ranging between about 0.5 and about 2.5 mole equivalents, preferably between about 0.75 and about 1.25 equivalents, per molar equivalent of total $NH_2$ group in the amino acid.

The reaction is quenched by adjusting the pH of the mixture with a suitable acid, e.g., concentrated hydrochloric acid, until the pH reaches between about 2 and about 3. The mixture separates on standing at room temperature to form a transparent upper layer and a white or off-white precipitate. The upper layer is discarded, and the modified amino acid is collected from the lower layer by filtration or decantation. The crude modified amino acid is then dissolved in water at a pH ranging between about 9 and about 13, preferably between about 1 1 and about 13. Insoluble materials are removed by filtration and the filtrate is dried in vacuo. The yield of modified amino acid generally ranges between about 30 and about 60%, and usually about 45%.

If desired, amino acid esters, such as, for example benzyl, methyl, or ethyl esters of amino acid compounds, may be used to prepare the modified amino acids of the invention. The amino acid ester, dissolved in a suitable organic solvent such as dimethylformamide, pyridine, or tetrahydrofuran is reacted with the appropriate amino modifying agent at a temperature ranging between about 5° C. and about 70° C., preferably about 25° C., for a period ranging between about 7 and about 24 hours. The amount of amino modifying agent used relative to the amino acid ester is the same as described above for amino acids. This reaction may be carried out with or without a base such as, for example, triethylamine or diisopropylethylamine.

Thereafter, the reaction solvent is removed under negative pressure and the ester functionality is removed by hydrolyzing the modified amino acid ester with a suitable alkaline solution, e.g. 1N sodium hydroxide, at a temperature ranging between about 50° C. and about 80° C., preferably about 70° C., for a period of time sufficient to hydrolyze off the ester group and form the modified amino acid having a free carboxyl group. The hydrolysis mixture is then cooled to room temperature and acidified, e.g. aqueous 25% hydrochloric acid solution, to a pH ranging between about 2 and about 2.5. The modified amino acid precipitates out of solution and is recovered by conventional means such as filtration or decantation. Benzyl esters may be removed by hydrogenation in an organic solvent using a transition metal catalyst.

The modified amino acid may be purified by recrystallization or by fractionation on solid column supports. Suitable recrystallization solvent systems include acetonitrile, methanol and tetrahydrofuran. Fractionation may be performed on a suitable solid column supports such as alumina, using methanol/n-propanol mixtures as the mobile phase; reverse phase column supports using trifluoroacetic acid/acetonitrile mixtures as the mobile phase; and ion exchange chromatography using water as the mobile phase. When anion exchange chromatography is performed, preferably a subsequent 0–500 mM sodium chloride gradient is employed.

In an alternate method modified amino acids having the formula:

CXXIV

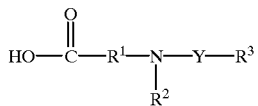

wherein

Y is C

$R^1$ is $C_3$–$C_{24}$ alkyl, $C_2$–$C_{20}$ alkenyl, $C_2$–$C_{20}$ alkyne, cycloalkyl, or aromatic;

$R^2$ is hydrogen, $C_1$–$C_4$ alkyl, or $C_2$–$C_4$ alkenyl; and $R^3$ is $C_1$–$C_7$ alkyl, $C_3$–$C_{10}$ cycloalkyl, aryl, thienyl, pyrrolo, or pyridyl, where $R^3$ is optionally substituted by one or more $C_1$–$C_5$ alkyl group, $C_2$–$C_4$ alkenyl group, F, Cl, OH, $SO_2$, COOH or, $SO_3H$; may be prepared by (a) reacting in water and the presence of a base a compound having the formula:

CXXV

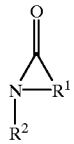

with a compound having the formula:

$R^3$—Y—X, wherein

Y, $R^1$, $R^2$, and $R^3$ are as above and X is a leaving group.

Compound CXXV can be prepared, for example by the method described in Olah et al., *Synthesis*, 537–538 (1979).

Compound XXXI was prepared as described in Scheme I from 10-undecen-1-ol, 1, by a three step procedure in an overall yield of 31%. Alkylation of phthalimide with alkanol, 1, under Mitsunobu conditions, followed by reaction with hydrazine gave 1-aminoundec-10-ene, 2, in 66% yield. The amine was derivatized with O-acetylsalicyloyl chloride and the resulting alkene, 3, was oxidized to the acid using potassium permanganate. Removal of the acetate, followed by acid precipitation provided compound XXXI in 47% yield based on amine 2.

Scheme I

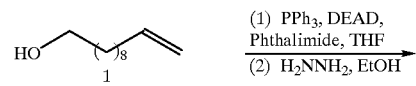

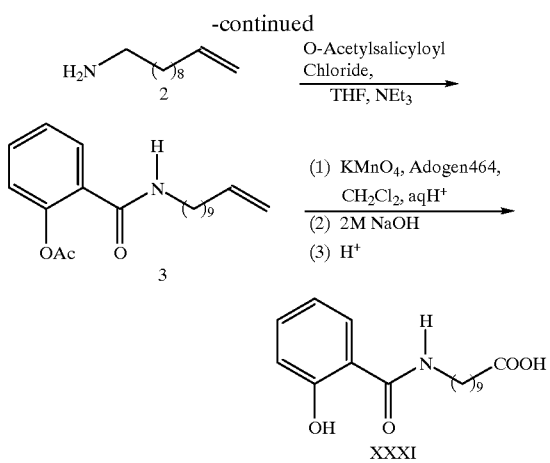

Delivery Systems

The compositions of the present invention may include one or more active agents.

In one embodiment, compounds I–CXXIII or poly amino acids or peptides that include at least one of these compounds may be used directly as a delivery carrier by simply mixing one or more compound, poly amino acid or peptide with the active agent prior to administration.

In an alternative embodiment, the compounds, poly amino acids, or peptide may be used to form microspheres containing the active agent. These compounds, poly amino acids, or peptides are particularly useful for the oral administration of certain biologically-active agents, e.g., small peptide hormones, which, by themselves, do not pass or only a fraction of the administered dose passes through the gastro-intestinal mucosa and/or are susceptible to chemical cleavage by acids and enzymes in the gastrointestinal tract.

If the modified amino acids, poly amino acids, or peptides are to be converted into microspheres, the mixture is optionally heated to a temperature ranging between about 20 and about 50° C., preferably about 40° C., until the modified amino acid(s) dissolve. The final solution contains between from about 1 mg and to about 2000 mg of compound, poly amino acid, or peptide per mL of solution, preferably between about 1 and about 500 mg per mL. The concentration of active agent in the final solution varies and is dependent on the required dosage for treatment. When necessary, the exact concentration can be determined by, for example, reverse phase HPLC analysis.

When the compounds, poly amino acids, or peptides are used to prepare microspheres, another useful procedure is as follows: Compounds, poly amino acids, or peptides are dissolved in deionized water at a concentration ranging between about 75 and about 200 mg/ml, preferably about 100 mg/ml at a temperature between about 25° C. and about 60° C., preferably about 40° C. Particulate matter remaining in the solution may be removed by conventional means such as filtration.

Thereafter, the compound, poly amino acid, or peptide solution, maintained at a temperature of about 40° C., is mixed 1:1 (V/V) with an aqueous acid solution (also at about 40° C.) having an acid concentration ranging between about 0.05 N and about 2 N, preferably about 1.7 N. The resulting mixture is further incubated at 40° C. for a period of time effective for microsphere formation, as observed by light microscopy. In practicing this invention, the preferred order of addition is to add the compound, poly amino acid, or peptide solution to the aqueous acid solution.

Suitable acids for microsphere formation include any acid which does not (a) adversely effect the modified amino acids, poly amino acids, or peptides e.g., initiate or propagate chemical decomposition;
(b) interfere with microsphere formation;
(c) interfere with microsphere incorporation of the active agent cargo; and
(d) adversely interact with the active agent cargo.

Preferred acids for use in this aspect include acetic acid, citric acid, hydrochloric acid, phosphoric acid, malic acid and maleic acid.

A microsphere stabilizing additive may be incorporated into the aqueous acid solution or into the compound or cargo solution prior to the microsphere formation process. With some active agents the presence of such additives promotes the stability and/or dispersibility of the microspheres in solution.

The stabilizing additives may be employed at a concentration ranging between about 0.1 and 5% (w/v), preferably about 0.5% (w/v). Suitable, but non-limiting, examples of microsphere stabilizing additives include gum acacia, gelatin, methyl cellulose, polyethylene glycol, polypropylene glycol, carboxylic acids and salts thereof, and polylysine. The preferred stabilizing additives are gum acacia, gelatin and methyl cellulose.

Under the above conditions, the compound molecules, poly amino acids, or peptides form hollow or solid matrix type microspheres wherein the cargo is distributed in a carrier matrix or capsule type microspheres encapsulating liquid or solid cargo. If the compound, poly amino acid, or peptide microspheres are formed in the presence of a soluble material, e.g., a pharmaceutical agent in the aforementioned aqueous acid solution, this material will be encapsulated within the microspheres. In this way, one can encapsulate pharmacologically active materials such as peptides, proteins, and polysaccharides as well as charged organic molecules, e.g., antimicrobial agents, which normally have poor bioavailability by the oral route. The amount of pharmaceutical agent which may be incorporated by the microsphere is dependent on a number of factors which include the concentration of agent in the solution, as well as the affinity of the cargo for the carrier. The compound, poly amino acid, or peptide microspheres do not alter the physiological and biological properties of the active agent. Furthermore, the encapsulation process does not alter the pharmacological properties of the active agent. Any pharmacological agent can be incorporated within the microspheres. The system is particularly advantageous for delivering chemical or biological agents which otherwise would be destroyed or rendered less effective by conditions encountered within the body of the animal to which it is administered, before the microsphere reaches its target zone (ie., the area in which the contents of the microsphere are to be released) and for delivering pharmacological agents which are poorly absorbed in the gastro-intestinal tract. The target zones can vary depending upon the drug employed.

The particle size of the microsphere plays an important role in determining release of the active agent in the targeted area of the gastro-intestinal tract. The preferred microspheres have diameters between about ≦0.1 microns and about 10 microns, preferably between about 0.5 microns and about 5 microns. The microspheres are sufficiently small to release effectively the active agent at the targeted area within the gastrointestinal tract such as, for example, between the stomach and the jejunum. Small microspheres can also be administered parenterally by being suspended in an appropriate carrier fluid (e.g., isotonic saline) and injected directly into the circulatory system, intramuscularly or subcutaneously. The mode of administration selected will vary, of course, depending upon the requirement of the active agent being administered. Large amino acid microspheres (>50 microns) tend to be less effective as oral delivery systems.

The size of the microspheres formed by contacting compounds, poly amino acids, or peptides with water or an aqueous solution containing active agents can be controlled by manipulating a variety of physical or chemical parameters, such as the pH, osmolarity or ionic strength of the encapsulating solution, size of the ions in solution and by the choice of acid used in the encapsulating process.

The administration mixtures are prepared by mixing an aqueous solution of the carrier with an aqueous solution of the active ingredient, just prior to administration. Alternatively, the carrier and the biologically or chemically active ingredient can be admixed during the manufacturing process. The solutions may optionally contain additives such as phosphate buffer salts, citric acid, acetic acid, gelatin, and gum acacia.

Stabilizing additives may be incorporated into the carrier solution. With some drugs, the presence of such additives promotes the stability and dispersibility of the agent in solution.

The stabilizing additives may be employed at a concentration ranging between about 0.1 and 5% (W/V), preferably about 0.5% (W/V). Suitable, but non-limiting, examples of stabilizing additives include gum acacia, gelatin, methyl cellulose, polyethylene glycol, carboxylic acids and salts thereof, and polylysine. The preferred stabilizing additives are gum acacia, gelatin and methyl cellulose.

The amount of active agent is an amount effective to accomplish the purpose of the particular active agent. The amount in the composition typically is a pharmacologically or biologically effective amount. However, the amount can be less than a pharmacologically or biologically effective amount when the composition is used in a dosage unit form, such as a capsule, a tablet or a liquid, because the dosage unit form may contain a multiplicity of carrier/biologically or chemically active agent compositions or may contain a divided pharmacologically or biologically effective amount. The total effective amounts can then be administered in cumulative units containing, in total, pharmacologically or biologically or chemically active amounts of biologically or pharmacologically active agent.

The total amount of active agent, and particularly biologically or chemically active agent, to be used can be determined by those skilled in the art. However, it has surprisingly been found that with some biologically or chemically active agents, the use of the presently disclosed carriers provides extremely efficient delivery, particularly in oral, intranasal, sublingual, intraduodenal, or subcutaneous systems. Therefore, lower amounts of biologically or chemically active agent than those used in prior dosage unit forms or delivery systems can be administered to the subject, while still achieving the same blood levels and therapeutic effects.

The amount of carrier in the present composition is a delivery effective amount and can be determined for any particular carrier or biologically or chemically active agent by methods known to those skilled in the art.

Dosage unit forms can also include any of excipients; diluents; disintegrants; lubricants; plasticizers; colorants; and dosing vehicles, including, but not limited to, water, 1,2-propane diol, ethanol, olive oil, or any combination thereof.

Administration of the present compositions or dosage unit forms preferably is oral or by intraduodenal injection.

The delivery compositions of the present invention may also include one or more enzyme inhibitors. Such enzyme inhibitors include, but are not limited to, compounds such as actinonin or epiactinonin and derivatives thereof. These compounds have the formulas below:

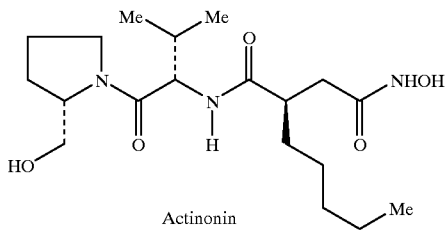

Actinonin CXXVI

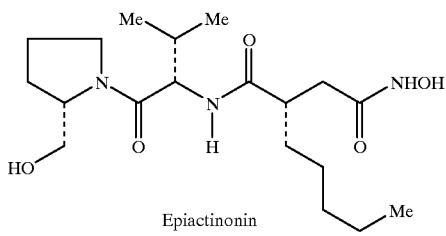

Epiactinonin CXXVII

Derivatives of these compounds are disclosed in U.S. Pat. No. 5,206,384. Actinonin derivatives have the formula:

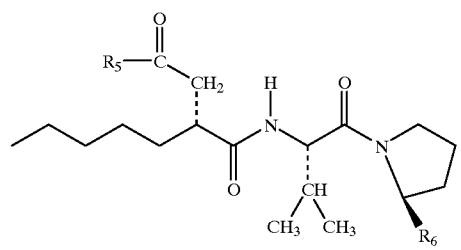

CXXVIII wherein $R^5$ is sulfoxymethyl or carboxyl or a substituted carboxy group selected from carboxamide, hydroxyaminocarbonyl and alkoxycarbonyl groups; and $R^6$ is hydroxyl, alkoxy, hydroxyamino or sulfoxyamino group. Other enzyme inhibitors include, but are not limited to, aprotinin (Trasylol) and Bowman-Birk inhibitor.

The compounds and compositions of the subject invention are useful for administering biologically or chemically active agents to any animals such as birds; mammals, such as primates and particularly humans; and insects. The system is particularly advantageous for delivering chemically or biologically or chemically active agents which would otherwise be destroyed or rendered less effective by conditions encountered before the active agent its target zone (i.e. the area in which the active agent of the delivery composition are to be released) and within the body of the animal to which they are administered. Particularly, the compounds and compositions of the present invention are useful in orally administering active agents, especially those which are not ordinarily orally deliverable.

DESCRIPTION OF THE PREFERRED EMBODIMENTS

The following examples illustrate the invention without limitation. All parts are given by weight unless otherwise indicated.

Example 1

Compound XIX was prepared as follows:

A 3 L three-neck round bottom flask was fitted with an overhead mechanical stirrer and a thermometer, and the flask was cooled in an ice-bath. A solution of 8-aminocaprylic acid (100.0 g, 0.65 moles) in 2 M aqueous sodium hydroxide (1.4 L) was charged into the round bottom flask. The temperature of the solution was kept at about 5° C., and O-acetylsalicyloyl chloride (198.6 g, 0.76 moles, 1.2 equiv.) was added portionwise over 7 hours. The mixture was stirred at 5° C. for 12 hours to yield a yellow homogenous solution. The solution was acidified with 1 M hydrochloric acid to pH 6.8 and was extracted with ethyl acetate (2×600 mL). The pH of the aqueous layer was readjusted to 6.3 and was further extracted with ethyl acetate (2×600 mL). The organic layers were combined, dried over anhydrous sodium sulfate, filtered, and evaporated under reduced pressure. The residue was redissolved in a minimum volume of 2 M aqueous sodium hydroxide, and the pH of the solution was between 9.5 and 10. The mixture was acidified with stirring with 1 M hydrochloric acid to pH of about 6.2, and a solid was formed. The solid was filtered, washed with water (3×300 mL), and recrystallized from 55% methanol/water (v/v) to yield Compound XVIII as an off-white solid (99.7 g, 57%).

Properties are listed below.

mp 116–117° C. $^1$H NMR (300 MHz, DMSO-$d_6$) δ: 12.70 (1H, br s), 11.95 (1H, br s) 8.81 (1H, t), 7.82 (1H, m), 7.38 (1H, m), 6.84 (2H, m), 2.36 (2H, q), 2.18 (2H, t), 1.50 (4H, br m), 1.28 (6H, m), Anal. Calcd for $C_{15}H_{21}NO_4$: C, 64.50; H, 7.58; IN, 5.02. Found: C, 64.26; H, 7.81; N, 4.93.

Similar procedures were used to prepare Compounds I, II, III, IV, VI, IX, X, XI, XII, XIII, XIV, XX, XXI, XXIII, XXVII, XXVIII, XXXIII, and XXXIV.

Properties are listed below.

Compound I: $^1$H NMR (300 MHz, $D_2O$): δ1.5 (2H, m) 2.0 (2H, t) 2.3 (2H,t) 7.5 (2H, t) 7.6 (1H, m) 7.3 (2H, m)

Compound II: $^1$H NMR (300 MHz, $D_2O$): δ1.4 (8H, m) 1.7 (6H, m) 2.1 (2H,t) 1.25 (1H, m) 3.05 (2H, t)

Compound III: $^1$H NMR (300 MHz, DMSO-$d_6$): δ0.7 (3H, m) 0.9 (2H, m) 1.1 (3H,q) 1.6 (5H, m) 1.75 (2H, q) 2.1 (2H, t) 3.0 (2H, q) 7.9 (1H,m)

Compound IV: Anal. Calcd for $C_{11}H_{13}NO_4$: C, 59.9; H, 5.87; N, 6.27; Found: C, 58.89; H, 5.85; N, 6.07. $^1$H NMR (300 MHz, DMSO-$d_6$): δ1.8 (2H, m) 2.3 (2H, t) 3.1 (2H,q) 6.9 (2H, t) 7.4 (1H, t) 7.8 (1H, d) 8.85 (1H, t) 12.0 (1H, s) 12.15 (1H, s)

Compound VI: $^1$H NMR (300 MHz, $D_2O$): δ0.8 (2H, m) 1.1 (4H, m) 1.4 (2H,q) 1.6 (7H, m) 2.15 (4H, m) 3.1 (2H, t)

Compound IX: $^1$H NMR (300 MHz, DMSO-$d_6$): δ0.9 (q, 3H), 1.2 (m, 7H), 1.3 (q, 2H), 1.5 (q, 3H), 1.9 (d, 2H), 2.0 (d, 1H), 2.2 (t, 2H), 3.0 (q, 3H), 7.7 (s, 1H)

Compound X: $^1$H NMR (300 MHz, DMSO-$d_6$): δ0.7(d, 2H), 0.9 (dd, 1H), 1.2–1.3 (m, 7H), 1.5 (q, 3H), 1.6–1.8 (m, 5H), 2.15 (t, 2H), 3.0 (m, 3H), 7.5 (s, 1H), 12.0 (s, 1H)

Compound XI: Anal. Calcd for $C_{15}H_{20}NO_3Cl$: C, 60.48; H, 6.78; N, 4.70; Found: C, 60.4; H, 6.68; N, 4.53. $^1$H NMR (300 MHz, DMSO-$d_6$): δ1.28 (m, 6H) 1.48 (m, 4H) 2.19 (t, 2H) 3.19 (qt, 2H), 7.323–7.48 (m, 4H), 8.39 (t, 1H), 12.09 (s, 1H)

Compound XII: Anal. Calcd for $C_{17}H_{22}NO_3$: C, 66.42; H, 7.23; N, 4.56; Found: C, 65.80; H, 7.17; N, 4.14. $^1$H NMR (300 MHz, DMSO-$d_6$): δ1.25 (m, 6H) 1.43–1.49 (m, 4H) 2.18 (t, 2H) 3.15 (qt, 2H), 6.72 (d, 1H), 7.21–7.26 (m, 2H), 7.39 (t, 1H), 7.48 (d, 1H), 7.65 (t, 1H), 8.21 (t, 1H)

Compound XIII: Anal. Calcd for $C_{15}H_{19}NO_3$: C, 60.18; H, 6,41; N, 4.67; Found: C, 60.26; H, 6.53; N, 4.61. $^1$H NMR (300 MHz, DMSO-$d_6$): δ1.28 (m, 6H), 1.45–1.52 (m, 4H), 2.19 (t, 2H), 2.22 (qt, 2H), 7.13 (m, 2H), 7.43–7.53 (m, 1H), 8.67 (t, 1H) 12.03 (s, $_1$H)

Compound XIV: Anal. Calcd for $C_{14}H_{20}N_2O_3$: .0.66 $H_2O$: C, 63.04; H, 7.91; N, 10.34 Found: C, 63.21; 7.59; 10.53. $^1$H NMR (300 MHz, DMSO-$d_6$): δ1.22–12.8 (m, 6H), 1.48–1.50 (m, 4H), 2.18 (t, 2H), 3.24 (qt, 2H), 7.48 (m, 1H), 8.15 (d, 1H), 8.63–8.69 (m, 2H), 8.97 (d, 1H)

Compound XX: Anal. Calcd for $C_{15}H_{20}NO_3F$: C, 60.09; H, 7.19; N, 4.98; Found: C, 63.82; H, 7.23; N, 4.94. $^1$H NMR (300 MHz, DMSO-$d_6$): δ1.28 (m, 6H) 1.49 (m, 4H) 2.19 (t, 2H) 3.23 (qt, 2H), 7.24–7.30 (m, 2H), 7.49–7.60 (m, 2H), 11.99 (s, 1H)

Compound XXI: Anal. Calcd for $C_{17}H_{23}NO_4$: C, 66.85; H, 7.61; N, 4.58; Found: C, 66.81; H, 7.69; N, 4.37. $^1$H NMR (300 MHz, DMSO-$d_6$): δ1.26 (m, 6H) 1.42–1.50(m, 4) 2.18 (t, 2H) 3.13 (qt, 2H), 6.63 (d, 1H), 6.80 (t, 1H), 6.86 (d, 1H), 7.15 (t, 1H), 7.39 (d, 1H), 7.60 (d, 1H), 8.03 (t, 1H), 9,95 (s, $_1$H), 12.12 (s, $_1$H)

Compound XXIII: Anal. Calcd for $C_{15}H_{27}NO_3$: C, 66.86; H, 10.22; N, 5.19; Found: C, 66.92; H, 10.72; N, 5.14. $^1$H NMR (300 MHz, DMSO-$d_6$): δ1.56–1.34 (m, 13H) 1.46 (t, 2H) 1.60–1.68 (m, 5H), 2.04 (t, 1H), 2.17 (t, 2H), 2.97 (qt, 2H), 7.62 (t, 1H), 11.98 (s, 1H)

Compound XXVII: Anal. Calcd for $C_{18}H_{27}NO_4$: C, 67.25; H, 8.48; N, 4.36; Found: C, 67.23; H, 8.57; N, 4.20. $^1$H NMR (300 MHz, DMSO-$d_6$): δ1.22–1.26 (m, 12H) 1.45–1.51 (m, 4H) 2.16 (t, 2H) 3.25 (qt, 2H), 6.85 (t, 2H), 7.37 (t, 1H), 7.81 (d, 1H), 8.79 (t, 1H), 11.95 (s, 1H), 12.72 (s, 1H)

Compound XXVIII: $^1$H NMR (300 MHz, DMSO-$d_6$): δ1.26 (8H, br m), 1.49 (4H, m), 2.17 (2H, t), 3.26 (2H, m), 6.86 (2H, m), 7.37 (1H, m), 7.83 (1H, m), 8.80 (1H, t), 11.95 (1H, s), 12.73 (1H, s).

Compound XXXIII: $^1$H NMR (300 MHz, DMSO-$d_6$): δ1.2 (a, 2H), 1.3 (q,2H), 1.3 (q, 2H), 1.5 (q, 2H), 2.2 (t, 2H), 3.0 (q, 2H), 3.5 (s, 2H), 7.3 (m, 5H), 8.0 (s, 1H)

Compound XXXIV: Anal. Calcd for $C_{12}H_{17}NO_4$: C, 62.23; H, 6.83; N, 5.57; Found: C, 61.93; H, 6.80; N, 5.56. $^1$H NMR (300 MHz, DMSO-$d_6$): δ1.24–1.34 (m, 2H) 1.49–1.57 (m, 4H) 2.19 (t, 2H) 3.26 (qt, 2H), 6.68 (t, 2H), 7.37 (s, 1H), 7.83 (d, 1H) 8.81 (t, 1H), 12.08 (s, 1H), 12.72 (s, 1H)

Example 1A

An alternate synthesis of compound XIX was as follows:

A 5 L three-neck round bottom flask was fitted with a heating mantle, an overhead mechanical stirrer, an addition funnel, and a thermometer. The reaction was performed under an argon atmosphere. Hydroxylamine-O-sulfonic acid (196.7 g, 1.74 moles, 1.10 equiv.) and formic acid (1 L) were charged into the round bottom flask and stirred to form a white slurry. A solution of cyclooctanone (200.0 g 1.58 moles, 1.0 equiv.) in formic acid (600 mL) was added dropwise to the white slurry via the addition funnel. After the addition, the addition funnel was replaced by a reflux condenser, and the reaction was heated to reflux (internal temperature about 105° C.) for 1 hour to give a brown solution. After the solution was cooled to room temperature, it was poured into a mixture of saturated aqueous ammonium chloride (1.5 L) and water (1.5 L). The aqueous mixture was extracted with chloroform (3×1200 mL). The combined chloroform layers were transferred into a beaker, and saturated sodium bicarbonate (2 L) was added slowly. The chloroform layer was then separated, dried over anhydrous sodium sulfate, and evaporated under reduced pressure to afford a brown oil. The oil was placed in a 500 mL round bottom flask with a magnetic stirrer. The round bottom flask was placed in a silicon oil bath and was fitted with a short path vacuum distillation head equipped with a thermometer. A Cow-type receiver was connected to three 250 mL flasks. 2-Azacyclononanone (145 g, 65%, mp 64–69° C.) was obtained by vacuum distillation (fraction with head temperature range from 80 to 120° C. at pressures between 3.0 and 3.4 mmHg).

A 5 L three-neck round bottom flask was fitted with a heating mantle, an overhead mechanical stirrer, a reflux condenser, and a 29 thermometer. A suspension of 2-azacyclononanone (83 g, 0.59 moles, 1.0 equiv.) in 5 M aqueous sodium hydroxide (650 mL, 3.23 moles, 5.5 equiv.) was charged into the round bottom flask. The mixture was heated to reflux (internal temperature about 110° C.) for 4 hours to yield a clear yellow solution. The heating mantle and reflux condenser were removed. After the solution cooled to room temperature, it was diluted with water (650 mL) and cooled further in an ice bath. Finely ground O-acetylsalicyloyl chloride (114.7 g, 0.59 moles, 1.0 equiv.) was added portionwise to the solution with stirring and continued cooling over 1 hour. After an additional 30 minutes, the ice-bath was removed and stirring was continued at ambient temperature for 21 hours to give a brownish yellow solution. The stirred mixture was acidified with 2 M sulfuric acid (about 850 mL) to a pH of about 1, and a yellow solid was formed. The solid was collected by filtration and was dissolved in warm methanol (1.7 L). Activated charcoal (about 5 g) was added to the methanol, and the solution was stirred for 10 minutes. The activated charcoal was removed by filtration, and the charcoal residue was washed with additional 300 mL methanol. Water (2 L) was added to the combined filtrates (i.e. the 2 L methanol), and an off-white solid precipitated upon standing at 4° C. overnight. The crude product was filtered and was recrystallized from 65% methanol/water (v/v) to yield Compound XIX (69.1 g, 42%) as off-white solid.

Properties are listed below:

mp 116–117° C.; HPLC, $^1$H NMR and Anal. Calcd for $C_{15}H_{21}NO_4$: C, 64.50; H, 7.58; N, 5.02. Found: C, 64.26; H, 7.81; N, 4.93.

Example 2

Compound XXXI was prepared as follows:

1-Aminoundec-10-ene. A mixture of 10-undecene-1-ol (5.00 g, 29.36 mmol, 1 equiv), triphenylphosphine (7.70 g, 29.36 mmol, 1 equiv) and phthalimide (4.32 g, 29.36 mmol, 1 equiv) in dry tetrahydrofuran (THF, 30 mL) was stirred vigorously under argon. Diethyl azodicarboxylate (DEAD, 5.11 g, 29.36 mmol, 1 equiv) was diluted with THF (12 mL) and added dropwise by syringe. After the addition, the reaction was stirred at room temperature for 4 hours. The solvent was evaporated under vacuum and ether (30 mL) was added to precipitate the triphenylphosphine oxide and hydrazine dicarboxylate which were removed by filtration. The precipitate was rinsed with ether (2×30 mL) and the combined filtrates were evaporated to afford a yellow solid. The yellow solid was triturated with warm hexanes (3×50 mL) and filtered. The combined hexanes were evaporated to give 1-phthalimidylundec-10-ene as a yellow wax.

The yellow wax was dissolved in an ethanolic solution (38 mL) of hydrazine hydrate (1.47 g, 1 equiv, 29.36 mmol). The mixture was heated at reflux for 2 hours. After the mixture was cooled to room temperature, concentrated hydrochloric acid (30 mL) was added and the solid was filtered through a sintered glass filter. The residue was washed with water (50 mL) and the combined filtrates were evaporated to provide a yellow solid. The yellow solid was redissolved in 1 M NaOH (100 mL) and extracted with ether (2×50 mL). The ether was dried and evaporated to provide a yellow oil. The oil was purified by Kugelrohr distillation (ca. 0.1 mmHg, 100° C.) to provide 1-aminoundec-10-ene (2) as a light yellow oil (3.29 g, 66%).

Properties are listed below.

$^1$H NMR (300 mHz, DMSO-$d_6$); δ1.23 (14H, br m), 1.99 (2H, m), 2.48 (2H, m), 4.94 (2H, m), 5.77 (1H, m).

1-(O-Acetylsalicyloylamino)undec-10-ene. O-Acetylsalicyloyl chloride (3.82 g, 19.25 mmol, 1 equiv) in THF (30 mL) was cooled in an ice bath. Triethylamine (1.95 g, 19.25 mmol, 1 equiv), followed by 1-aminoundec-10-ene (3.26 g, 19.25 mmol, 1 equiv) in THF (10 mL) were added via syringe. The ice bath was removed and the reaction was stirred at room temperature for 3.5 hours. After removal of the solvent, the residue was dissolved in EtOAc (50 mL) and washed with water (2×30 mL). The organic layer was dried and evaporated to afford 1-(O-acetylsalicyloylamino)undec-10-ene as a colorless oil, in a quantitative yield, 6.59 g.

Properties are listed below.

$^1$H NMR (300 mHz, DMSO-$d_6$: δ1.26 (12H, br s), 1.47 (2H,m), 1.99(2H,m), 2.19 (3H,s), 3.15 (2H, q), 4.95 (2H, m), 5.78 (1H, m), 7.15 (1H, m), 7.30 (1H, m), 7.50 (2H, m) 8.24 (1H, t).

COMPOUND XXXI 1-(O-Acetylsalicyloylamino)under-10-ene (6.59 g, 19.25 mmol, 1 equiv) in dichloromethane (108 mL) was added to a mixture of water (108 mL), sulfuric acid (9M, 13 mL), glacial acetic acid (2.16 mL) and methyltrialkyl($C_8$–$C_{10}$) ammonium chloride (0.32 g) (Adogen® 464, available from Aldrich Chemical Co.). The mixture was stirred vigorously in an ice bath and potassium permanganate (9.13 g, 57.75 mmol, 3 equiv) was added in portions over 1.5 hours. After the addition, the ice bath was removed and the resultant purple solution was stirred at room temperature for 20 hours. The solution was cooled in an ice bath and sodium bisulfite (6.8 g) was added to dissipate the excess permanganate. The organic layer was separated and the aqueous layer was extracted with ethyl acetate (2×50 mL). The combined organic layers were washed with brine (50 mL), dried and evaporated. Sodium hydroxide (2M, 50 mL) was added to the residue and stirred for 30 min. The solution was diluted with water (50 mL), washed with ether (50 mL) and acidified to pH 1 with 2M hydrochloric acid. A solid formed and was collected by filtration. Recrystallization of the solid from 65% MeOH/$H_2O$ gave XXXI as a tan solid (2.78 g, 47% based on the amine).

Properties are listed below.

$^1$H NMR (300 mHz, DMSO-$d_6$): δ1.24 (10H, br m), 1.51 (4H, m), 2.17 (2H, t), 3.27 (2H, m), 6.86 (2H, m), 7.37 (1H m), 7.82 (1H, m), 8.80 (1H, t), 11.95 (1H, s), 12.72 (1H, s).

Example 3

Compound LXXXVI was prepared as follows:

A one liter three-neck round bottom flask was fitted with a magnetic stirrer and a condenser. A solution of 3-(4-aminophenyl)propionic acid (30 g, 0.182 moles) in methylene chloride (300 mL) was charged to the flask and trimethylsilyl chloride (46.2 mL, 0.364 moles) was added in one portion. The reaction mixture was refluxed for 1.5 hours, allowed to cool to room temperature, and then immersed in an ice/water bath. Triethylamine (76.2 mL, 0.546 moles)

was added, followed by 2-methoxycinnamoyl chloride (35.8 g, 0.182 moles). The reaction mixture was allowed to warm to room temperature and then stirred for 48 hours. The solvent was removed by rotary evaporation and saturated sodium bicarbonate solution and ethyl acetate were added to the residue. The layers were separated, the aqueous layer was acidified to pH 1.4 with 2N aqueous sulfuric acid and extracted with ethyl acetate (2×400 mL). The combined organic extracts were concentrated in vacuo and the residue recrystallized from 50% (v/v) aqueous methanol to provide the product as a tan solid (48.57 g, 82%).

Properties are listed below.

$^1$H NMR (300 MHz, DMSO-$d_6$): δ12.1 (1H, br), 7,8 (1H, dd), 7.6 (3H, m), 7.4 (1H, m), 7.3 (2H, m), 7.1 (1H, d), 7.0 (1H, t), 6.9 (1H, d), 3.9 (3H, s), 2.8 (2H, t), 2.5 (4H, m). Anal. Calcd for $C_{19}H_{19}NO_4$: C, 70.14; H, 5.88; N, 4.31. Found: C, 69.76; H, 5.91; N, 4.21.

Example 4

Compound CXVII was prepared as follows:

A 3 L three-neck round bottom flask was fitted with an overhead mechanical stirrer and a thermometer. A solution of 8-aminocaprylic acid (10.0 g, 0.054 moles) in 2 M aqueous sodium hydroxide (1.4 L) was charged into the round bottom flask and O-nitrobenzoyl chloride (12.0 g, 0.065 moles, 1.2 equiv.) was added portionwise over 7 h. The mixture was stirred at 25° C. for 12 h to afford a yellow homogenous solution. The solution was acidified with 1 M hydrochloric acid to about pH 2, an oily residue separated and was decanted. The oil was dissolved in stirred water (300 mL) and cooled in and ice/water bath. The product precipitated as a white solid. The solid was filtered, washed with water (3×300 mL), and recrystallized from 55% acetonitrile/water (v/v) to provide Compound CXVII as an off-white solid (7.4 g, 47%). mp 89–92° C.

Properties are listed below.

$^1$H NMR (300 MHz, DMSO-$d_6$) δ: 12.0 (1H, s), 8.65 (1H, t), 8.0 (1H, dd), 7.8 (1H, m), 7.65 (1H, m), 7.5 (1H, m), 3.2 (2H, q), 2.2 (2H, t), 1.5 (4H, br m), 1.3 (6H, br m). Anal. Calcd for $C_{15}H_{20}N_2O_5$: C, 58.41; H, 6.54; N, 9.09. Found: C, 58.50; H, 6.71; N, 9.14.

The other compounds of the invention can be readily prepared by following the procedures described in Examples 1–4.

Examples 5–15

In Vivo Evaluation of Recombinant Growth Hormone in Rats

Dosing compositions were prepared by mixing the modified amino acids and recombinant human growth hormone (rhGH) as listed in Table 1 below in a phosphate buffer solution at a pH of about 7–8.

Rats were administered the dosing composition by sublingual, oral gavage, intraduodenal administration, or colonic administration. Delivery was evaluated by using an ELISA assay for rhGH from Medix Biotech, Inc. For intracolonic administration, a sample was prepared and dosed to fasted rats at 25 mg/kg of carrier in a buffered solution containing propylene glycol (0–50%) and 1 mg/kg rhGH.

Results are illustrated in Table 1 below.

Comparative Example 5A rhGH (6 mg/ml) was administered by oral gavage to a rat, and delivery valuated according to the procedure of Example 5.

Results are illustrated in Table 1 below.

TABLE 1

In Vivo Delivery of rhGH

| Example | Carrier | Carrier Dose (mg/kg) | Drug Dose (mg/kg) | Method of Administration | Mean Peak Serum Levels of rhGH (ng/mL) |
| --- | --- | --- | --- | --- | --- |
| 5 | I | 500 | 6 | oral | 26.6 +/− 43.83 |
| 5A | none | 0 | 6 | oral | <10 +/− 10 |
| 6 | V | 500 | 6 | oral | 3.22 +/− 7.2 |
| 7 | VI | 500 | 6 | oral | 19.34 +/− 18.73 |
| 8 | VIII | 500 | 6 | oral | 73.41 +/− 70.3 |
| 9 | IX | 500 | 6 | oral | 28.70 +/− 41.7 |
| 10 | XIII | 25 | 1 | colonic | 109.52 +/− 36.1 |
| 11 | XIX | 200 | 3 | oral | 60.92 +/− 26.3 |
| 12 | XIX | 25 | 1 | colonic | 111.52 +/− 16.4 |
| 13 | XIX | 100 | 3 | sublingual | 119.14 +/− 65.6 |
| 14 | XIX | 25 | 1 | intranasal | 92.7 +/− 73.2 |
| 15 | XXVII | 25 | 1 | colonic | 73.72 +/− 4.9 |

Examples 16–27

In Vivo Evaluation of Recombinant Growth Hormone in Rats Preparation of Dosing Solutions The delivery agents were reconstituted with distilled water and adjusted 7.2–8.0 with either aqueous hydrochloric acid or aqueous sodium hydroxide. A stock solution of rhGH was prepared by mixing rhGH, D-mannitol and glycine and dissolving this mixture in 2% glycerol/water. The stock solution was then added to the delivery agent solution. Several delivery agent to active agent ratios were studied.

In Vivo Experiments

Male Sprague-Dawley rats weighing 200–250 g were fasted for 24 hours and administered ketamine (44 mg/kg) and chlorpromazine (1.5 mg/kg) 15 minutes prior to dosing. The rats were administered one of the dosing solutions described above by subcutaneous injection, intranasal instillation, or sublingual instillation. Blood samples were collected serially from the tail artery for serum calcium concentration determination or serum rhGH concentrations. The dose of rhGH administered in these experiments was 0.1 mg/kg.

Serum rhGH concentrations were quantified by an rhGH enzyme immunoassay test kit. The results are given in Table 2 and FIGS. 1 and 2.

In FIG. 2 the circles represent the response following SL dosing of an aqueous solution of compound CXXIII and rhGH. The squares represent the response following IN dosing of an aqueous solution of compound CXXIII and rhGH. The triangles represent the response following IC dosing of an aqueous solution of compound CXXIII and rhGH. The dose of compound CXXIII was 25 mg/kg and the dose of rhGH was 1 mg/kg.

Comparative Example 16A rhGH (1 mg/kg) was administered by oral gavage to a rat, and delivery was evaluated according to the procedure of Example 16.

Results are illustrated in Table 2 below.

TABLE 2

Delivery Agent Enhancement of Recombinant Human Growth Hormone (rhGH) Bioavailability Administered by Subcutaneous Administration.

| Example | Deliver Ageny | Delivery Agent Dose (mg/kg) | Peak Serum [rhGH] (ng/mL) |
|---|---|---|---|
| 16 | CXXIII | 1.0 | 22 ± 3 |
| 16A | None | 0.0 | 4 ± 2 |
| 17 | CXXIII | 2.5 | 25 ± 5 |
| 18 | CXXIII | 25 | 30 ± 6 |
| 19 | CXI | 2.5 | 16 ± 2 |
| 20 | LVIII | 1.0 | 29 ± 10 |
| 21 | LXXXVI | 1.0 | 22 ± 7 |
| 22 | LXXXVI | 2.5 | 23 ± 5 |
| 23 | LXI | 2.5 | 26 ± 5 |
| 24 | CX | 1.0 | 15 ± 3 |
| 25 | CXV | 1.0 | 25 ± 3 |
| 26 | LXVI | 1.0 | 33 ± 5 |
| 27 | CIX | 1.0 | 16 ± 3 |

Examples 28–33

In Vivo Evaluation of Interferon in Rats

Dosing compositions were prepared by mixing the modified amino acid compounds and interferon a2b as listed in Table 3 below in a Trizma® hydrochloride buffer solution (Tris-HCl) at a pH of about 7–8. Propylene glycol (0–25%) was added as a solubilizing agent, if necessary.

Rats were administered the dosing composition by oral gavage, intraduodenal administration, or intracolonic administration. Delivery was evaluated by use of an ELISA assay for human interferon a from Biosource, Inc.

Results of intracolonic administration are illustrated in Table 3 below.

Comparative Example 28A

Interferon α2b (250 μg/kg) was administered intracolonically to rats, and delivery was evaluated according to the procedure of Example 14.

Results are illustrated in Table 3 below.

TABLE 3

In Vivo Delivery of Interferon by Intracolonic Administration

| Example | Carrier | Carrier Dose (mg/kg) | Interferon Dose (μg/kg) | Mean Peak Serum Levels of Interferon (pg/mL) |
|---|---|---|---|---|
| 28 | VII | 100 | 250 | 5241 +/− 2205 |
| 28A | none | 0 | 250 | 0 |
| 29 | XI | 100 | 250 | 1189 +/− 1373 |
| 30 | XII | 100 | 250 | 6955 +/− 2163 |
| 31 | XIX | 100 | 250 | 11193 +/− 8559 |
| 32 | XXI | 100 | 250 | 4238 +/− 2789 |
| 33 | XXXIV | 100 | 250 | 4853 +/− 5231 |

Examples 34–37

In Vivo Evaluation of Salmon Calcitonin in Rats

Dosing compositions were prepared by mixing the modified amino acids and salmon calcitonin as listed in Table 4 below. 400 mg of carrier were added to 2.9 mL of 25% aqueous propylene glycol. The resultant solution was stirred, and the pH was adjusted to 7.2 with sodium hydroxide (1.0 N). Water was added to bring the total volume to 2.0 mL. The sample had a final carrier concentration of 200 mg/mL. Calcitonin (10 μg) was added to the solution. The total calcitonin concentration was 25 μg/mL.

For each sample a group of fasted rats were anesthetized. The rats were administered the dosing composition by oral gavage, intracolonic instillation, or intraduodenal administration. Blood samples were collected serially from the tail artery. Serum calcium was determined by testing with a Calcium Kit (Sigma Chemical Company, St. Louis, Mo., USA).

Results are illustrated in Table 4 below.

TABLE 4

In Vivo Delivery of Calcitonin

| Example | Carrier | Carrier Dose (mg/kg) | Drug Dose (μg/kg) | Method of Administration | Maximum Decrease in Serum Calcium (% below baseline) |
|---|---|---|---|---|---|
| 34 | I | 400 | 10 | oral | |
| 35 | V | 400 | 10 | oral | 18.35 +/− 2.87 |
| 36 | XIX | 10 | 3 | intracolonic | 26.49 +/− 12.3 |
| 37 | XIX | 200 | 7.5 | oral | 25.48 +/− 4.7 |

Examples 38–43

In Vivo Evaluation of Salmon Calcitonin in Rats
Preparation of Dosing Solution

The delivery agents were reconstituted with distilled water and adjusted to pH 7.2–8.0 with either aqueous hydrochloric acid or aqueous sodium hydroxide. A stock solution of sCT was prepared by dissolving sCT in citric acid (0.085N). The stock solution was then added to the delivery agent solution. Several different delivery agent to active agent ratios were studied.

In Vivo Experiments

Male Sprague-Dawley rats weighing 200–250 g were fasted for 24 hours and administered ketamine (44 mg/kg) and chlorpromazine (1.5 mg/kg) 15 minutes prior to dosing. The rats were administered one of the dosing solutions described above by subcutaneous injection. Blood samples were collected serially from the tail artery for serum calcium concentration.

Serum calcium concentrations were quantified by the o-cresolphthalein complexone method (Sigma) using a UV/VIS spectrophotometer (Perkin Elmer). The results are given in Table 5.

Examples 38A

Salmon calcitonin was administered by oral gavage to rats, and delivery was evaluated according to the Procedure of Example 38. The results are given in Table 5 below.

TABLE 5

Delivery Agent Enhancement of Salmon Calcitonin (sCT, dosed at 0.2 μg/kg) Bioavailability Administered by Subcutaneous Administration.

| Example | Deliver Ageny | Delivery Agent Dose (μg/kg) | Percent Decrease in Serum Calcium |
|---|---|---|---|
| 38 | CXXIII | 2 | 17 ± 3 |
| 38A | None | 0 | 17 ± 2 |
| 39 | CXXIII | 20 | 25 ± 4 |
| 40 | CXXIII | 200 | 25 ± 5 |
| 41 | CXXIII | 2000 | 26 ± 5 |
| 42 | CXI | 20 | 21 ± 4 |
| 43 | CXIV | 20 | 20 ± 3 |

Examples 44–50

In Vivo Evaluation of Heparin in Rats

Dosing compositions were prepared by mixing the modified amino acids and heparin as listed in Table 4. In a test tube, 900 mg of carrier were dissolved in 3 mL of propylene glycol, and 0.299 g of sodium heparin was dissolved in 3 mL of water. The solutions were mixed by vortex. Sodium hydroxide (10M) was added to the resulting mixture until a solution was obtained. The pH was then adjusted to 7.4+/−0.5 with concentrated hydrochloric acid, and the final solution was sonicated at 40° C. for 30 minutes.

A group of fasted, conscious rats were administered the dosing compositions by oral gavage. Blood samples were collected by cardiac puncture following the administration of ketamine (44 mg/kg)., Heparin activity was determined by utilizing the activated partial thromboplastim time (APTT) according to the method of Henry, J. B., *Clinical Diagnosis and Management by Laboratory Methods*; Philadelphia, Pa.; W B Saunders (1979).

Results are illustrated in Table 6 below.

Comparative Example 44A

Heparin (100 mg/kg) was administered by oral gavage to rats, and heparin activity was determined according to the procedure of Example 44.

Results are illustrated in Table 6 below.

TABLE 6

In Vivo Delivery of Heparin by Oral Administration

| Example | Carrier | Carrier Dose (mg/kg) | Drug Dose (mg/kg) | Mean Peak APTT (sec) |
|---|---|---|---|---|
| 44 | II | 300 | 100 | 25.45 +/− 2.8 |
| 44A | none | none | 100 | 20.7 +/− 0.17 |
| 45 | III | 300 | 100 | 38.64 +/− 17 |
| 46 | V | 300 | 100 | 87.4 +/− 34.1 |
| 47 | XII | 300 | 100 | 49.53 +/− 17.1 |
| 48 | XIX | 300 | 100 | 119.99 +/− 56.3 |
| 49 | XXXI | 50 | 25 | 127.56 +/− 22.97 |
| 50 | XXXI | 50 | 10 | 50.85 +/− 9.1 |

Example 51

The method of Example 44 was followed, substituting low molecular weight heparin for the heparin and varying the amounts of propylene glycol and water for solubilization as, necessary.

Examples 50–58

In vivo Evaluation of Parathyroid Hormone in Rats Preparation of Dosing Solutions The delivery agents were reconstituted with distilled water and/or propylene glycol and adjusted to an apparent pH of 7.2–8.0 with either aqueous hydrochloric acid or aqueous sodium hydroxide. A stock solution of parathyroid hormone was prepared by dissolving parathyroid hormone in water. The parathyroid hormone solution was then added to the delivery agent solution. Several different delivery agent to active agent ratios were studied.

In Vivo Experiments

Male Sprague-Dawley rats weighing 200–250 g were fasted for 24 hours and administered ketamine (44 mg/kg) and chlorpromazine (1.5 mg/kg) 15 minutes prior to dosing. The rats were administered one of the dosing solutions described above by oral gavage or intracolonic instillation. Blood samples were collected serially from the tail artery for serum determination of parathyroid hormone concentration. Serum parathyroid hormone concentrations were quantified by a parathyroid hormone radioimmunoassay test kit.

In Vivo Oral Administration

Oral administration of solutions containing parathyroid hormone (PTH) and the non-α-amino acid delivery agents was tested in vivo in rats. The result show a significant increase in the oral bioavailability of parathyroid hormone as compared to similar administration of the active agent alone. Data are presented in Table 7.

TABLE 7

Delivery Agent Enhancement of Parathyroid Hormone (PTH) Oral Bioavailability.

| Example | Carrier | Carrier Dose mg/kg | Method of Administration | Active Agent Dose (μg/kg) | Peak Serum [PTH] (pg/mL) |
|---|---|---|---|---|---|
| 51 | CXXIII | 100 | intracolonic | 25 | 130 ± 20 |
| 52 | CXXIII | 250 | oral | 100 | 75 ± 25 |
| 53 | CXXIII | 250 | oral | 25 | 20 ± 6 |
| 54 | CVIII | 100 | intracolonic | 25 | 115 ± 20 |

TABLE 7-continued

Delivery Agent Enhancement of Parathyroid Hormone (PTH) Oral Bioavailability.

| Example | Carrier | Carrier Dose mg/kg | Method of Administration | Active Agent Dose (µg/kg) | Peak Serum [PTH] (pg/mL) |
|---|---|---|---|---|---|
| 55 | LXXXVI | 100 | intracolonic | 25 | 40 ± 12 |
| 56 | LVIII | 100 | intracolonic | 25 | 145 ± 25 |
| 57 | CXIV | 100 | intracolonic | 25 | 65 ± 15 |
| 58 | LXXXIX | 100 | intracolonic | 25 | 70 ± 15 |

The above mentioned patents, applications, test methods, and publications are hereby incorporated by reference in their entirety.

Many variations of the present invention will suggest themselves to those skilled in the art in light of the above detailed description. All such obvious variations are within the full intended scope of the appended claims.

What is claimed is:

1. A pharmacological composition comprising:
   (A) at least one biologically-active agent selected from the group consisting of human growth hormone, bovine growth hormone, growth hormone-releasing hormone, an interferon, interleukin-1, interleukin-II, insulin, heparin, low molecular weight heparin, calcitonin, erythropoietin, atrial naturetic factor, an antigen, a monoclonal antibody, somatostatin, adrenocorticotropin, gonadotropin releasing hormone, oxytosin, vasopressin, cromolyn sodium, vancomycin, desferrioxamine, an antimicrobial, an antifungal agent, and combinations thereof; and
   (B) at least one carrier compound having the formula:

2-HO—Ar—CONR$^8$—R$^7$—COOH wherein Ar is an unsubstituted phenyl or naphthyl;
   $R^7$ is selected from the group consisting of $C_4$ to $C_{20}$ alky, $C_4$ to $C_{20}$ alkenyl, phenyl, naphthyl, ($C_1$ to $C_{10}$ alkenyl) phenyl, ($C_1$ to $C_{10}$ alkyl)naphthyl, ($C_1$ to $C_{10}$ alkenyl) naphthyl, phenyl ($C_1$ to $C_{10}$ alkenyl), naphthyl ($C_1$ to $C_{10}$ alkyl), and naphthyl ($C_1$ to $C_{10}$ alkenyl);
   $R^8$ is selected from the group consisting of hydrogen, $C_1$ to $C_4$ alkyl, $C_1$ to $C_4$ alkenyl, hydroxy, and $C_1$ to $C_4$ alkoxy;
   $R^7$ is optionally substituted with $C_1$ to $C_4$ alkyl, $C_1$ to $C_4$ alkenyl, $C_1$ to $C_4$ alkoxy, —OH, —SH and —CO$_2$R$^9$ or any combination thereof;
   $R^9$ is hydrogen, $C_1$ to $C_4$ alkyl or $C_1$ to $C_4$ alkenyl;
   $R^7$ is optionally interrupted by oxygen, nitrogen, sulfur or any combination thereof;
   with the proviso that the compounds are not substituted with an amino group in the position alpha to the acid group;
   or salts thereof.

2. The composition according to claim 1, wherein said biologically-active agent comprises calcitonin.

3. The composition according to claim 1, wherein $R^7$ is selected from the group consisting of $C_4$ to $C_{20}$ alkyl and $C_4$ to $C_{20}$ alkenyl.

4. The composition according to claim 1, wherein $R^7$ is selected from the group consisting of $C_5$ to $C_{20}$ alkyl and $C_5$ to $C_{20}$ alkenyl.

5. The composition according to claim 1 wherein the carrier has the formula:

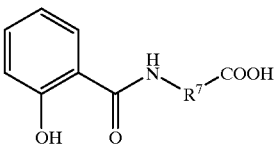

or salts thereof.

6. A dosage unit form comprising:
   (A) a pharmacological composition according to claim 3; and
   (B)
   (a) an excipient,
   (b) a diluent,
   (c) a disintegrant,
   (d) a lubricant,
   (e) a plasticizer,
   (f) a colorant,
   (g) a dosing vehicle, or
   (h) any combination thereof.

7. A dosage unit form according to claim 6, comprising a tablet, a capsule, or a liquid.

8. A dosage unit form according to claim 7, wherein said dosing vehicle is selected from the group consisting of water, 1,2-propane diol, ethanol or any combination thereof.

9. A method for administering a biologically-active agent to a mammal in need of said agent, said method comprising administering orally to said mammal a composition as defined in claim 3.

10. A method for administering a biologically-active agent to an animal in need of said agent, said method comprising administering orally to said mammal a composition as defined in claim 3.

11. The composition according to claim 3, wherein said biologically-active agent comprises human growth hormone.

12. The composition according to claim 3, wherein said biologically-active agent comprises heparin.

13. The composition according to claim 3, wherein said biologically-active agent comprises low molecular weight heparin.

14. The composition according to claim 3, wherein said biologically-active agent comprises parathyroid hormone.

15. The composition according to claim 3, wherein said biologically-active agent comprises insulin.

16. A pharmacological composition comprising:
   (A) at least one biologically active agent;
   (B) at least one carrier compound having the formula:

2-HO—Ar—CONR$^8$—R$^7$—COOH or salts thereof,
   wherein Ar is unsubstituted phenyl
   $R^7$ is selected from the group consisting of $C_4$ to $C_{20}$ alkyl, $C_4$ to $C_{20}$ alkenyl, phenyl, naphthyl, ($C_1$ to $C_{10}$ alkenyl)phenyl, ($C_1$ to $C_{10}$ alkyl)naphthyl, ($C_1$ to $C_{10}$ alkenyl)naphthyl, phenyl($C_1$ to $C_{10}$ alkenyl), naphthyl ($C_1$ to $C_{10}$ alkyl), naphthyl($C_1$ to $C_{10}$ alkenyl);
   $R^8$ is hydrogen;
   $R^7$ is optionally substituted with $C_1$ to $C_4$ alkyl, $C_1$ to $C_4$ alkenyl, $C_1$ to $C_4$ alkoxy, —OH, —SH and —CO$_2$R$^9$ or any combination thereof;
   $R^9$ is hydrogen, $C_1$ to $C_4$ alkyl or $C_1$ to $C_4$ alkenyl;
   $R^7$ is optionally interrupted by oxygen, nitrogen, sulfur or any combination thereof;

with the proviso that the compounds are not substituted with an amino group in the position alpha to the acid group.

17. The composition according to claim 16, wherein $R^7$ is selected from the group consisting of $C_4$ to $C_{20}$ alkyl and $C_4$ to $C_{20}$ alkenyl.

18. The composition according to claim 17, wherein $R^7$ is selected from the group consisting of $C_5$ to $C_{20}$ alkyl and $C_5$ to $C_{20}$ alkenyl.

19. The composition according to claim 17, wherein the biologically active agent comprises human growth hormone, bovine growth hormone, growth hormone-releasing hormone, an interferon, interleukin-1, interleukin-II, insulin, heparin, low molecular weight heparin, calcitonin, erythropoietin, atrial naturetic factor, an antigen, a monoclonal antibody, somatostatin, adrenocorticotropin, gonadotropin releasing hormone, oxytosin, vasopressin, cromolyn sodium, vancomycin, desferrioxamine, an antimicrobial, an antifungal agent, or a combination thereof.

20. The composition according to claim 19, wherein said biologically-active agent comprises human growth hormone, an interferon, insulin, heparin, low molecular weight heparin, calcitonin, erythropoietin, cromolyn sodium, desferrioxamine and combinations thereof.

21. The composition according to claim 20, wherein said biologically-active agent comprises calcitonin.

22. The composition according to claim 20, wherein said biologically-active agent comprises human growth hormone.

23. The composition according to claim 20, wherein said biologically-active agent comprises heparin.

24. The composition according to claim 20, wherein said biologically-active agent comprises low molecular weight heparin.

25. The composition according to claim 20, wherein said biologically-active agent comprises insulin.

26. A dosage unit form comprising:
(A) a pharmacological composition according to claim 17; and
(B)
(i) an excipient,
(ii) a diluent,
(iii) a disintegrant,
(iv) a lubricant,
(v) a plasticizer,
(vi) a colorant,
(vii) a dosing vehicle, or
(viii) any combination thereof.

27. A dosage unit form according to claim 26, comprising a tablet, a capsule, or a liquid.

28. A dosage unit form according to claim 26, wherein said dosing vehicle is selected from the group consisting of water, 1,2-propane diol, ethanol or any combination thereof.

29. A method for administering a biologically-active agent to a mammal in need of said agent, said method comprising administering orally to said mammal a composition as defined in claim 17.

30. A method for administering a biologically-active agent to an animal in need of said agent, said method comprising administering orally to said animal a composition as defined in claim 17.

31. The composition according to claim 16, wherein said carrier has the formula:

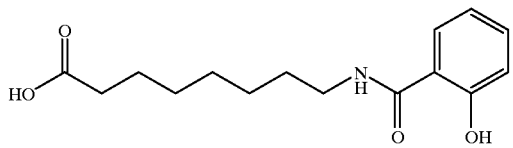

XIX or a salt thereof, and said biologically active agent is heparin.

32. The composition according to claim 16, wherein said carrier has the formula:

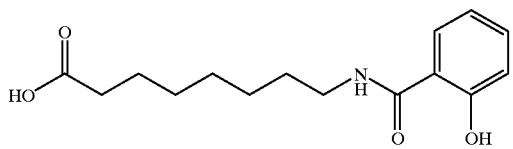

XIX or a salt thereof, and said biologically active agent is low molecular weight heparin.

33. The composition according to claim 16, wherein said carrier has the formula:

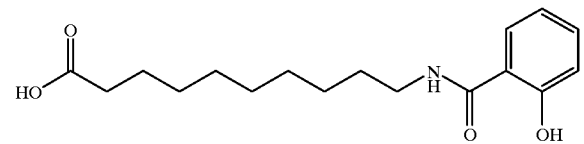

XXXI or a salt thereof, and said biologically active agent is heparin.

34. The composition according to claim 16, wherein said carrier has the formula:

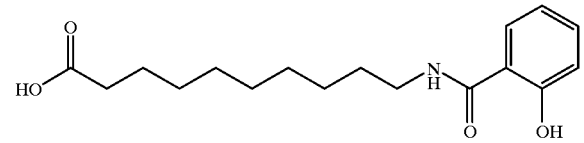

XXXI or a salt thereof, and said biologically active agent is low molecular weight heparin.

35. The composition according to claim 3, wherein said biologically-active agent comprises human growth hormone, an interferon, insulin, heparin, low molecular weight heparin, calcitonin, erythropoietin, cromolyn sodium, desferrioxamine or a combination thereof.

36. A pharmacological composition comprising:
(A) parathyroid hormone; and
(B) at least one carrier compound having the formula:

2-HO—Ar—CONR⁸—R⁷—COOH wherein Ar is an unsubstituted phenyl or naphthyl;
$R^7$ is selected from the group consisting of $C_4$ to $C_{20}$ alkyl, $C_4$ to $C_{20}$ alkenyl, phenyl, naphthyl, ($C_1$ to $C_{10}$ alkenyl)phenyl, ($C_1$ to $C_{10}$ alkyl)naphthyl, ($C_1$ to $C_{10}$ alkenyl)naphthyl, phenyl ($C_1$ to $C_{10}$ alkenyl), naphthyl ($C_1$ to $C_{10}$ alkyl), and naphthyl ($C_1$ to $C_{10}$ alkenyl);

$R^8$ is selected from the group consisting of hydrogen, $C_1$ to $C_4$ alkyl, $C_1$ to $C_4$ alkenyl, hydroxy, and $C_1$ to $C_4$ alkoxy;

$R^7$ is optionally substituted with $C_1$ to $C_4$ alkyl, $C_1$ to $C_4$ alkenyl, $C_1$ to $C_4$ alkoxy, —OH, —SH and —$CO_2R^9$ or any combination thereof;

$R^9$ is hydrogen, $C_1$ to $C_4$ alkyl or $C_1$ to $C_4$ alkenyl;

$R^7$ is optionally interrupted by oxygen, nitrogen, sulfur or any combination thereof;

with the proviso that the compounds are not substituted with an amino group in the position alpha to the acid group; or salts thereof.

37. The composition according to claim 36, wherein $R^7$ is selected from the group consisting of $C_4$ to $C_{20}$ alkyl and $C_4$ to $C_{20}$ alkenyl.

38. The composition according to claim 36, wherein $R^7$ is selected from the group consisting of $C_5$ to $C_{20}$ alkyl and $C_5$ to $C_{20}$ alkenyl.

39. The composition according to claim 36, wherein the carrier has the formula:

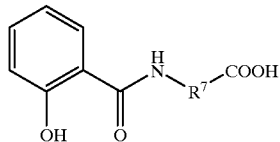

or salts thereof.

40. A dosage unit form comprising:
(A) a pharmacological composition according to claim 37; and
(B)
(i) an excipient,
(ii) a diluent,
(iii) a disintegrant,
(iv) a lubricant,
(v) a plasticizer,
(vi) a colorant,
(vii) a dosing vehicle, or
(viii) any combination thereof.

41. A dosage unit form according to claim 40, comprising a tablet, a capsule, or a liquid.

42. A dosage unit form according to claim 40, wherein said dosing vehicle is selected from the group consisting of water, 1,2-propane diol, ethanol or any combination thereof.

43. A method for administering parathyroid hormone to a animal in need thereof, said method comprising administering orally to said animal a composition as defined in claim 37.

44. A pharmacological composition comprising:
(A) at least one biologically active agent selected from the group consisting of human growth hormone, bovine growth hormone, growth hormone-releasing hormone, an interferon, interleukin-1, interleukin-II, insulin, heparin, low molecular weight heparin, calcitonin, erythropoietin, atrial naturetic factor, an antigen, a monoclonal antibody, somatostatin, adrenocorticotropin, gonadotropin releasing hormone, oxytosin, vasopressin, cromolyn sodium, vancomycin, desferrioxamine, an antimicrobial, an antifungal agent, and combinations thereof; and (B) at least one carrier compound having the formula:

2-HO—Ar—CONR$^8$—R$^7$—COOH or salts thereof,
wherein Ar is unsubstituted phenyl;
$R^7$ is selected from the group consisting of $C_4$ to $C_{20}$ alkyl, $C_4$ to $C_{20}$ alkenyl, phenyl, naphthyl, ($C_1$ to $C_{10}$ alkenyl)phenyl, ($C_1$ to $C_{10}$ alkyl)naphthyl, ($C_1$ to $C_{10}$ alkenyl)naphthyl, phenyl($C_1$ to $C_{10}$ alkenyl), naphthyl ($C_1$ to $C_{10}$ alkyl), naphthyl($C_1$ to $C_{10}$ alkenyl);

$R^8$ is hydrogen;

$R^7$ is optionally substituted with $C_1$ to $C_4$ alkyl, $C_1$ to $C_4$ alkenyl, $C_1$ to $C_4$ alkoxy, —OH, —SH and —$CO_2R^9$ or any combination thereof;

$R^9$ is hydrogen, $C_1$ to $C_4$ alkyl or $C_1$ to $C_4$ alkenyl;

$R^7$ is optionally interrupted by oxygen, nitrogen, sulfur or any combination thereof;

with the proviso that the compounds are not substituted with an amino group in the position alpha to the acid group.

45. A pharmacological composition comprising:
(A) parathyroid hormone; and
(B) at least one carrier compound having the formula:

2-HO—Ar—CONR$^8$—R$^7$—COOH or salts thereof,
wherein Ar is unsubstituted phenyl;
$R^7$ is selected from the group consisting of $C_4$ to $C_{20}$ alkyl, $C_4$ to $C_{20}$ alkenyl, phenyl, naphthyl, ($C_1$ to $C_{10}$ alkenyl)phenyl, ($C_1$ to $C_{10}$ alkyl)naphthyl, ($C_1$ to $C_{10}$ alkenyl)naphthyl, phenyl($C_1$ to $C_{10}$ alkenyl), naphthyl ($C_1$ to $C_{10}$ alkyl), naphthyl($C_1$ to $C_{10}$ alkenyl);

$R^8$ is hydrogen;

$R^7$ is optionally substituted with $C_1$ to $C_4$ alkyl, $C_1$ to $C_4$ alkenyl, $C_1$ to $C_4$ alkoxy, —OH, —SH and —$CO_2R^9$ or any combination thereof;

$R^9$ is hydrogen, $C_1$ to $C_4$ alkyl or $C_1$ to $C_4$ alkenyl;

$R^7$ is optionally interrupted by oxygen, nitrogen, sulfur or any combination thereof;

with the proviso that the compounds are not substituted with an amino group in the position alpha to the acid group.

46. A dosage unit form comprising:
(A) a pharmacological composition according to claim 1; and
(B)
(a) an excipient,
(b) a diluent,
(c) a disintegrant,
(d) a lubricant,
(e) a plasticizer,
(f) a colorant,
(g) a dosing vehicle, or
(h) any combination thereof.

47. A dosage unit form comprising:
(A) a pharmacological composition according to claim 4; and
(B)
(a) an excipient,
(b) a diluent,
(c) a disintegrant,
(d) a lubricant, (e) a plasticizer,
(f) a colorant,
(g) a dosing vehicle, or
(h) any combination thereof.

48. A dosage unit form comprising:
(A) a pharmacological composition according to claim 5; and
(B)
(a) an excipient,
(b) a diluent,
(c) a disintegrant,
(d) a lubricant,
(e) a plasticizer,
(f) a colorant,
(g) a dosing vehicle, or
(h) any combination thereof.

49. A method for preparing a pharmacological composition, said method comprising mixing:
(A) at least one biologically-active agent;
(B) at least one carrier compound according to claim 3, and
(C) optionally a dosing vehicle.

50. A method for preparing a pharmacological composition, said method comprising mixing:
(A) at least one biologically-active agent;
(B) at least one carrier compound according to claim 4; and
(C) optionally a dosing vehicle.

51. A method for preparing a pharmacological composition, said method comprising mixing:
(A) at least one biologically-active agent;
(B) at least one carrier compound according to claim 5; and
(C) optionally a dosing vehicle.

52. A method for administering a biologically-active agent to an animal in need of said agent, said method comprising administering orally to said mammal a composition as defined in claim 1.

53. A method for administering a biologically-active agent to an animal in need of said agent, said method comprising administering orally to said mammal a composition as defined in claim 4.

54. A method for administering a biologically-active agent to an animal in need of said agent, said method comprising administering orally to said mammal a composition as defined in claim 5.

* * * * *